(12) United States Patent
Asada et al.

(10) Patent No.: US 8,946,317 B2
(45) Date of Patent: Feb. 3, 2015

(54) COMPOSITION FOR HARD TISSUE REPAIR

(75) Inventors: Noriaki Asada, Mobara (JP); Shinya Aoki, Ichihara (JP); Hiroshi Naruse, Chiba (JP); Shoichi Miyakoshi, Sagamihara (JP); Masami Arata, Moriyama (JP)

(73) Assignee: Mitsui Chemicals. Inc., Minato-Ku, Tokyo (JP)

( * ) Notice: Subject to any disclaimer, the term of this patent is extended or adjusted under 35 U.S.C. 154(b) by 243 days.

(21) Appl. No.: 13/508,451

(22) PCT Filed: Nov. 18, 2010

(86) PCT No.: PCT/JP2010/070577
§ 371 (c)(1),
(2), (4) Date: May 7, 2012

(87) PCT Pub. No.: WO2011/062227
PCT Pub. Date: May 26, 2011

(65) Prior Publication Data
US 2012/0225012 A1    Sep. 6, 2012

(30) Foreign Application Priority Data

Nov. 20, 2009  (JP) ................ 2009-265648
Nov. 20, 2009  (JP) ................ 2009-265649

(51) Int. Cl.
*A61F 2/00*     (2006.01)
*A61L 27/54*    (2006.01)
*A61L 27/16*    (2006.01)
*C08F 265/06*   (2006.01)
*A61L 24/00*    (2006.01)
*A61L 24/06*    (2006.01)

(52) U.S. Cl.
CPC ............... *A61L 27/54* (2013.01); *A61L 27/16* (2013.01); *C08F 265/06* (2013.01); *A61L 24/0015* (2013.01); *A61L 24/06* (2013.01); *A61L 2300/404* (2013.01); *A61L 2430/02* (2013.01)
USPC .......................................... 523/115; 523/116

(58) Field of Classification Search
None
See application file for complete search history.

(56) References Cited

U.S. PATENT DOCUMENTS

| | | |
|---|---|---|
| 5,091,033 A | 2/1992 | Nakabayashi et al. |
| 5,264,215 A | 11/1993 | Nakabayashi et al. |
| 5,459,177 A | 10/1995 | Miyakoshi et al. |
| 5,461,124 A | 10/1995 | Ritter et al. |
| 5,530,038 A | 6/1996 | Yamamoto et al. |
| 5,866,632 A | 2/1999 | Hashimoto et al. |
| 5,981,621 A | 11/1999 | Clark et al. |
| 5,990,036 A | 11/1999 | Deviny |
| 6,051,626 A | 4/2000 | Zeng et al. |
| 2004/0110864 A1* | 6/2004 | Hecht et al. ............ 523/113 |
| 2005/0215660 A1 | 9/2005 | Tomikawa et al. |
| 2008/0171841 A1 | 7/2008 | Zeng et al. |

FOREIGN PATENT DOCUMENTS

| | | |
|---|---|---|
| CN | 1213285 A | 4/1999 |
| EP | 1 704 845 A1 | 9/2006 |
| JP | 62-286467 A | 12/1987 |
| JP | 4-189363 A | 7/1992 |
| JP | 7-097306 A | 4/1995 |
| JP | 9-110913 A | 4/1997 |
| JP | 10-114615 A | 5/1998 |
| WO | WO/03082931 | 10/2003 |

OTHER PUBLICATIONS

Office Action issued on Sep. 11, 2013, by the Russian Patent Office in corresponding Russian Patent Application No. 2012125204/15, and an English Translation of the Office Action (9 pages).
Australian Office Action dated May 2, 2013, issued in corresponding Australian Patent Application No. 2010320055 (5 pgs.).
Office Action issued on Nov. 6, 2013, by the Chinese Patent Office in corresponding Chinese Patent Application No. 201080048626.X. (8 pages).
International Search Report (PCT/ISA/210) issued on Jan. 25, 2011, by the Japanese Patent Office as the International Searching Authority for International Application No. PCT/JP2010/070577.
Kosuge et al., "Influence of PMMA Powder on Properties of MMA-TBB Resin Cement", The Journal of the Japanese Society for Dental Materials and Devices, 1999, pp. 347-351, vol. 18, No. 5 (partial English-translation included).
Kosuge, "Influence of PMMA Powder on Properties of MMA-TBB Resin Cement", The Journal of the Japanese Society for Dental Materials and Devices, 2000, pp. 92-101, vol. 19, No. 1 (partial English-translation included).
Kudou et al., "Addition of antibacterial agents to MMA-TBB dentin bonding systems—Influence on Tensile Bond Strength and Antibacterial Effect—" Dental Materials Journal, 2000, pp. 65-74, vol. 19, No. 1.
The Extended European Search Report dated Apr. 11, 2014, issued by the European Patent Office in corresponding European Application No. 10831620.9-1455 (6 pages).

* cited by examiner

*Primary Examiner* — James Rogers
(74) *Attorney, Agent, or Firm* — Buchanan, Ingersoll & Rooney PC

(57) ABSTRACT

The composition for hard tissue repair of the present invention is characterized by comprising 5 to 98.95 parts by weight of a monomer (A), 1 to 75 parts by weight of a (meth)acrylate polymer (B) and 0.05 to 20 parts by weight of a polymerization initiator composition (C) containing an organoboron compound (c1), with the proviso that the total amount of the components (A), (B) and (C) is 100 parts by weight. The composition undergoes small-scale heat generation during curing and can ensure a sufficient working time.

20 Claims, 2 Drawing Sheets

COMPOSITION FOR HARD TISSUE REPAIR

TECHNICAL FIELD

The present invention relates to a composition for hard tissue repair.

BACKGROUND ART

As bone cement for fixation of hard tissues, such as bones and cartilages, to artificial joints, bone filling materials used for osteoporosis therapy or the like, artificial bone materials, etc., various compositions for hard tissue repair have been studied in the past. For example, compositions containing polymethyl methacrylate, methyl methacrylate and benzoyl peroxide (polymerization initiator), compositions containing (meth)acrylate, an inorganic filler, such as calcium phosphate, and an organic peroxide, etc. have been studied (see, for example, patent literature 1).

Such compositions, however, undergo large-scale heat generation during curing and have a high risk of doing damage to the affected tissue.

When a composition for repair is used for hard tissues such as bones, it is a usual way that the components to form the composition are mixed in advance in a container or the like to prepare a composition and then the composition is applied to the surface of the affected part, taking into consideration workability, prevention of infection, etc. However, the state of the composition after mixing sometimes has influence on the workability during the application of the composition.

Since acrylic adhesives using an initiator containing an organoboron compound have low toxicity and low harmfulness and have high adhesive strength, development of them to dental applications has been promoted (see, for example, patent literature 2). However, if other medical applications, such as surgical applications, are intended, further improvement in handling stability or workability of the composition between mixing of the components and application to the application area has been sometimes required.

CITATION LIST

Patent Literature

Patent literature 1: Japanese Patent Laid-Open Publication No. 224294/1996
Patent literature 2: Japanese Patent Laid-Open Publication No. 110913/1997

SUMMARY OF INVENTION

Technical Problem

It is an object of the present invention to provide a composition for hard tissue repair, which undergoes small-scale heat generation during curing and has excellent workability.

Solution to Problem

In order to solve the above problems, the present inventors have earnestly studied compositions for hard tissue repair. The hard tissue repairs include adhesion between hard tissues, filling in hard tissues, adhesion between hard tissues and artificial substances, such as titanium, ceramics and stainless steel, adhesion between hard tissues and other tissues such as soft tissues, etc. In such repairs, adhesion between teeth and filling materials (i.e., dental use) is not included.

As a result, the present inventors have found that the above problems can be solved by a composition comprising specific amounts of a monomer, a (meth)acrylate polymer and a specific polymerization initiator composition, and they have accomplished the present invention.

That is to say, the composition for hard tissue repair of the present invention comprises 5 to 98.95 parts by weight of a monomer (A), 1 to 75 parts by weight of a (meth)acrylate polymer (B) and 0.05 to 20 parts by weight of a polymerization initiator composition (C) containing an organoboron compound (c1), with the proviso that the total amount of the components (A), (B) and (C) is 100 parts by weight.

The polymer (B) is preferably a polymer mixture which comprises polymer particles (b1) having a weight-average molecular weight of $30 \times 10^4$ to $60 \times 10^4$ and a specific surface area of 1.5 to 4.5 (m$^2$/g), polymer particles (b2) having a weight-average molecular weight of $5 \times 10^4$ to $20 \times 10^4$ and a specific surface area of 0.51 to 1.2 (m$^2$/g) and polymer particles (b3) having a weight-average molecular weight of $5 \times 10^4$ to $20 \times 10^4$ and a specific surface area of 0.1 to 0.5 (m$^2$/g), contains the polymer particles (b1) in an amount of 0 to 98% by weight, and contains the polymer particles (b2) and the polymer particles (b3) in the total amount of not less than 2% by weight based on the total weight of the polymer particles (b1), (b2) and (b3), with the proviso that the total amount of the polymer particles (b1), (b2) and (b3) is 100% by weight.

It is preferable that the polymerization initiator composition (C) contains an aprotic solvent (c2) having a boiling point of 30° C. to 150° C. in an amount of 30 to 80 parts by weight based on 100 parts by weight of the organoboron compound (c1). It is also preferable that the polymerization initiator composition (C) contains an aprotic solvent (c2') having a boiling point of 50° C. to 120° C. in an amount of 5 to 40 parts by weight and an alcohol (c3) having a boiling point of 60° C. to 180° C. in an amount of 0.2 to 5 parts by weight, based on 100 parts by weight of the organoboron compound (c1).

The composition for hard tissue repair preferably has a viscosity of 0.4 to 2,000,000 cp within 30 seconds after mixing of the components (A), (B) and (C).

The composition for hard tissue repair may further comprise, for example, a polymerization inhibitor (D), an ultraviolet light absorber, a flexibilizer and a plasticizer.

It is a preferred embodiment that the content of the polymerization inhibitor (D) is in the range of 10 to 5000 ppm based on the monomer (A).

The polymerization inhibitor (D) is preferably at least one substance selected from hydroquinone, dibutylhydroquinone, hydroquinone monomethyl ether, 2,6-di-tert-butylphenol, 2,6-di-tert-butyl-p-cresol, catechol, pyrogallol, benzoquinone, 2-hydroxybenzoquinone, p-methoxyphenol, t-butylcatechol, butylated hydroxyanisole, butylated hydroxytoluene and t-butylhydroquinone.

The composition for hard tissue repair may further comprise at least one substance selected from:
    anti-infectious agents, antibiotics, antibacterial agents, anti-virus agents, analgesics, compositions of analgesics, anorectic drugs, antihelmintic drugs, antiarthritic agents, antiasthmatic drugs, anticonvulsants, antidepressants, antidiuretics, antidiarrheal agents, antihistamine drugs, anti-inflammatory drugs, antimigraine drugs, antiemetic agents, antineoplastic drugs, antiparkinsonian agents, antipruritic drugs, antipsychotics, antipyretic drugs, antispasmodic drugs, anticholinergic agents, sympathomimetic agents, cardiovascular drugs, antiarrhythmic drugs, antihypertensive drugs, diuretics, vasodilators, immunosuppressant drugs, muscle-relaxant drugs, parasympatholytic drugs, stimulants, sedative drugs, tranquilizers, cholinergic agents, chemotherapeutic drugs, radio pharmaceuticals, bone inductive drugs, heparin neutralizer agents of static bladder, procoagulants, hemostatic agents, xanthine derivatives, hormones, proteins of natural origin or proteins synthesized by genetic engineering, polysaccharides, glycoproteins, lipoproteins, oligonucleotides, antibody, antigen, vasopressin, vasopressin analogs, epinephrine, selectin, clot promoting toxicants, plasminogen activating factor inhibitors, platelet activators, bone-forming factors, synthetic peptides having hemostatic action, and perfumes, such as orange oil, grapefruit oil, lemon oil, lime oil, clove oil, wintergreen oil, peppermint oil, peppermint spirit, banana distillate, cucumber distillate, honey distillate, rose water, menthol, anethole, alkyl salicylate, benzaldehyde, monosodium glutamate, ethylvanillin, thymol and vanillin.

A cured product, which is obtained from the composition for hard tissue repair, is given 24 hours after the preparation of the composition for hard tissue repair and has a thickness of not less than 0.1 μm, a length of not less than 25 mm and a width of not less than 2 mm, preferably has a flexural elastic modulus, as measured under the conditions of a test rate of 2 mm/min, of not less than 100 MPa and a tensile strength, as measured under the conditions of a test rate of 1 mm/min, of not less than 10 MPa.

The kit for hard tissue repair of the present invention has members in which the components of the monomer (A), the (meth)acrylate polymer (B) and the polymerization initiator composition (C) containing an organoboron compound, which are contained in the above composition for hard tissue repair, are encased in two or more divided groups in an optional combination.

The kit for hard tissue repair preferably has constitution in which the monomer (A), the polymer (B) and the polymerization initiator composition (C) are each independently encased, and the monomer (A) is first mixed with the polymerization initiator composition (C) containing an organoboron compound and subsequently mixed with the polymer (B).

When the kit further contains a polymerization inhibitor (D), the kit preferably has members in which the components of the monomer (A), the (meth) acrylate polymer (B), the polymerization initiator composition (C) containing an organoboron compound and the polymerization inhibitor (D), which are contained in the above composition for hard tissue repair, are encased in two or more divided groups in an optional combination.

The kit containing the polymerization inhibitor (D) preferably has constitution in which a mixture of the monomer (A) and the polymerization inhibitor (D), the polymer (B) and the polymerization initiator composition (C) are each independently encased, and the mixture of the monomer (A) and the polymerization inhibitor (D) is first mixed with the polymerization initiator composition (C) containing an organoboron compound and subsequently mixed with the polymer (B).

The kit may include a jig that is used for applying a composition for hard tissue repair obtained by mixing the components (A), (B) and (C) and the components added when needed to the affected part.

The jig is, for example, a brush, a fiber ball, a cloth, a sponge ball or a piece of sponge.

The kit may further contain an aqueous solution for pretreatment containing 1 to 15% by weight of citric acid and 1 to 5% by weight of iron(III) chloride.

Advantageous Effects of Invention

The composition for hard tissue repair of the present invention undergoes small-scale heat generation during curing, and besides, it has excellent workability.

DESCRIPTION OF EMBODIMENTS

Figure 1:
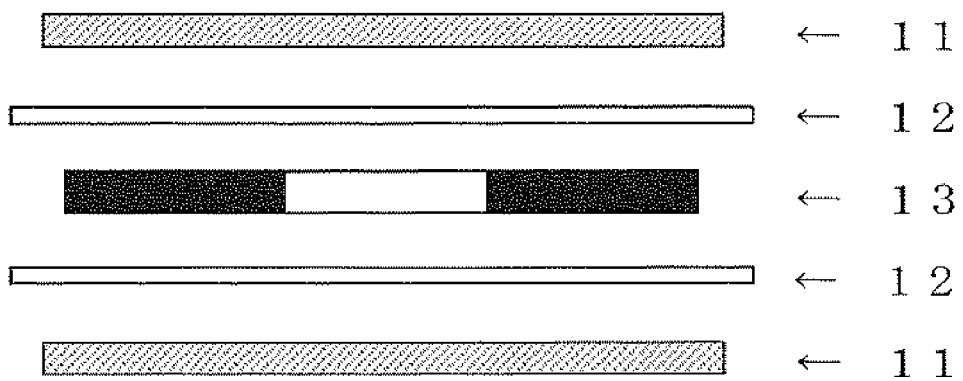
FIG. 1 is a schematic view showing an example of a process for preparing a sample of a cured product used in the examples of the present invention.

In the composition for hard tissue repair of the present invention, a monomer (A) is contained. As the monomer (A), any monomer can be used without specific restriction as long as it can be polymerized by the later-described polymerization initiator composition (C). As the monomer (A), any of a monofunctional monomer and a polyfunctional monomer can be used depending upon the use purpose.

Examples of the monomers (A) include methacrylates, acrylates and other vinyl compounds.

Of these monomers, at least one substance selected from acrylates and methacrylates is preferable from the viewpoint of relatively low irritation of the human body (acrylates and methacrylates are sometimes generically referred to as "(meth)acrylates" hereinafter).

Of the monomers (A), monomers having an acidic group are preferable from the viewpoint of excellent adhesion to hard tissues.

Therefore, use of a combination of a (meth)acrylate (having no acidic group) and a monomer having an acidic group as the monomer (A) is also a preferred embodiment.

Examples of the monofunctional (meth)acrylates (having no acidic group) include:

alkyl (meth)acrylates, such as methyl (meth)acrylate, ethyl (meth)acrylate, propyl (meth)acrylate, butyl (meth)acrylate, hexyl (meth)acrylate, 2-ethylhexyl (meth)acrylate, dodecyl(meth)acrylate, lauryl (meth)acrylate, cyclohexyl (meth)acrylate, benzyl (meth)acrylate and isobornyl (meth)acrylate;

hydroxyalkyl esters of (meth)acrylic acid, such as 2-hydroxyethyl (meth)acrylate, 2-hydroxypropyl (meth)acrylate, 3-hydroxypropyl (meth)acrylate, 4-hydroxybutyl (meth)acrylate, 5-hydroxypentyl (meth)acrylate, 6-hydroxyhexyl (meth)acrylate, 1,2-dihydroxypropyl mono(meth)acrylate, 1,3-dihydroxypropyl mono(meth)acrylate and erythritol mono(meth)acrylate;

polyalkylene glycol mono(meth)acrylates, such as diethylene glycol mono(meth)acrylate, triethylene glycol mono(meth)acrylate, polyethylene glycol mono(meth)acrylate and polypropylene glycol mono(meth)acrylate;

(poly)alkylene glycol monoalkyl ether (meth)acrylates, such as ethylene glycol monomethyl ether (meth)acrylate, ethylene glycol monoethyl ether (meth)acrylate, diethylene glycol monomethyl ether (meth)acrylate, triethylene glycol monomethyl ether (meth)acrylate, polyethylene glycol monomethyl ether (meth)acrylate and polypropylene glycol monoalkyl ether (meth)acrylate;

fluoroalkyl esters of (meth)acrylic acid, such as perfluorooctyl (meth)acrylate and hexafluorobutyl (meth)acrylate;

silane compounds having a (meth)acryloxyalkyl group, such as γ-(meth)acryloxypropyltrimethoxysilane and γ-(meth)acryloxypropyltri(trimethylsiloxy)silane; and (meth)acrylates having a heterocyclic ring, such as tetrahydrofurfuryl (meth)acrylate.

Examples of the polyfunctional (meth)acrylates (having no acidic group) include:

poly(meth)acrylates of alkanepolyols, such as ethylene glycol di(meth)acrylate, propylene glycol di(meth)acrylate, butylene glycol di(meth)acrylate, neopentyl glycol di(meth)acrylate, hexylene glycol di(meth)acrylate, trimethylolpropane tri(meth)acrylate and pentaerythritol tetra(meth)acrylate;

polyoxyalkane polyol poly(meth)acrylates, such as diethylene glycol di(meth)acrylate, triethylene glycol di(meth)acrylate, polyethylene glycol di(meth)acrylate, dipropylene glycol di(meth)acrylate, polypropylene glycol di(meth)acrylate, dibutylene glycol di(meth)acrylate and dipentaerythritol hexa(meth)acrylate;

alicyclic or aromatic di(meth)acrylates represented by the following formula (1):

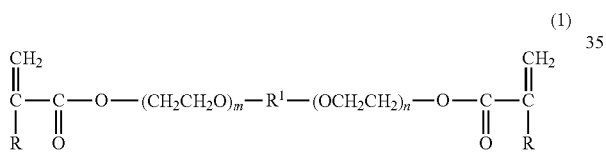

wherein R is a hydrogen atom or a methyl group, m and n are numbers of 0 to 10 which may be the same or different, and $R^1$ is any one of the following:

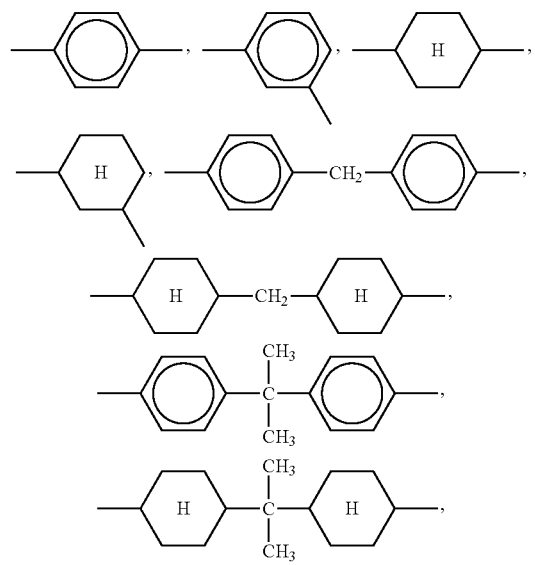

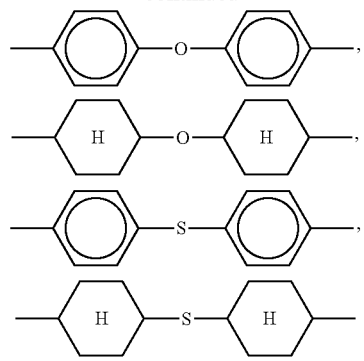

alicyclic or aromatic epoxy di(meth)acrylates represented by the following formula (2):

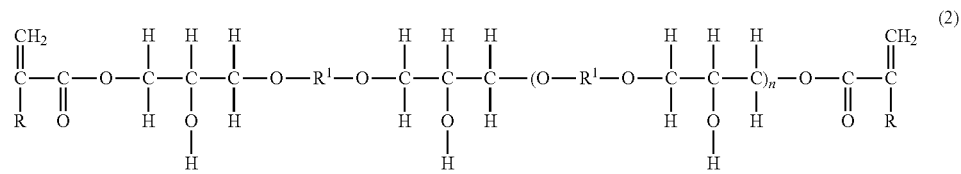

wherein R is a hydrogen atom or a methyl group, n is a number of 0 to 10, and $R^1$ is any one of the following:

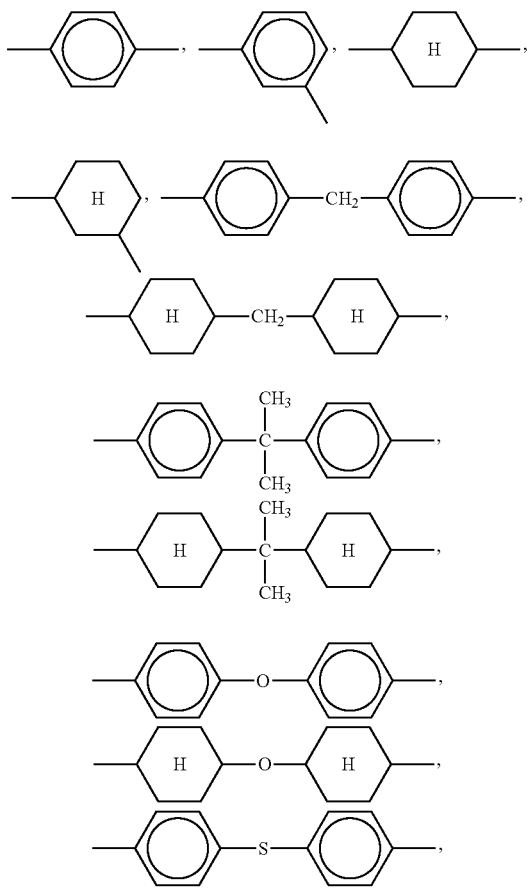

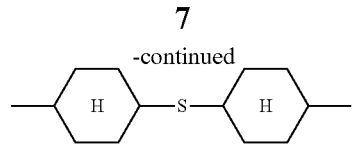

and
polyfunctional (meth)acrylates having a urethane bond in a molecule, which are represented by the following formula (3):

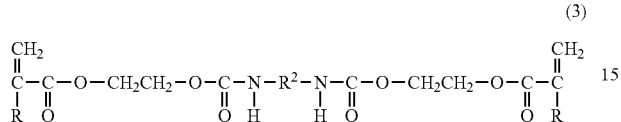

(3)

wherein R is a hydrogen atom or a methyl group, and $R^2$ is any one of the following:

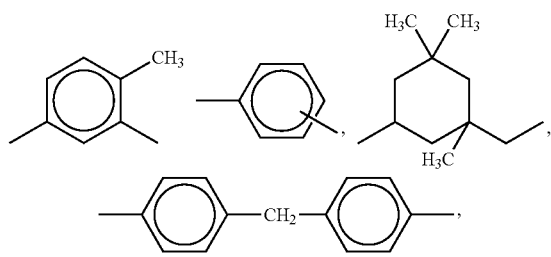

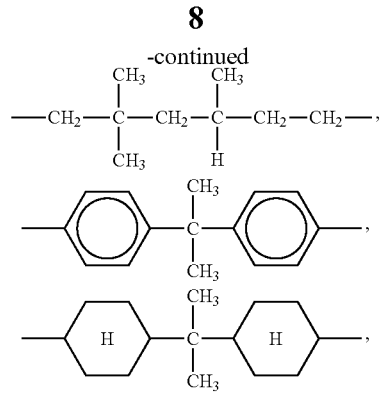

Of these (meth)acrylates, preferred monofunctional (meth)acrylates include:

- alkyl (meth)acrylates, such as methyl (meth)acrylate and ethyl (meth)acrylate;
- hydroxyalkyl esters of (meth)acrylic acid, such as 2-hydroxyethyl (meth)acrylate, 1,3-dihydroxypropyl mono (meth)acrylate and erythritol mono(meth)acrylate; and
- polyethylene glycol mono(meth)acrylates, such as triethylene glycol monomethyl ether (meth)acrylate and triethylene glycol mono(meth)acrylate.

Preferred polyfunctional (meth)acrylates include:

- di(meth)acrylates having an ethylene glycol chain in a molecule, such as triethylene glycol di(meth)acrylate and polyethylene glycol di(meth)acrylate;
- compounds represented by the following formula (1)-a:

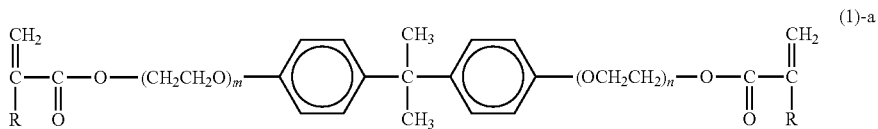

(1)-a wherein R is a hydrogen atom or a methyl group, and m and n are numbers of 0 to 10 which may be the same or different;

compounds represented by the following formula (2)-a:

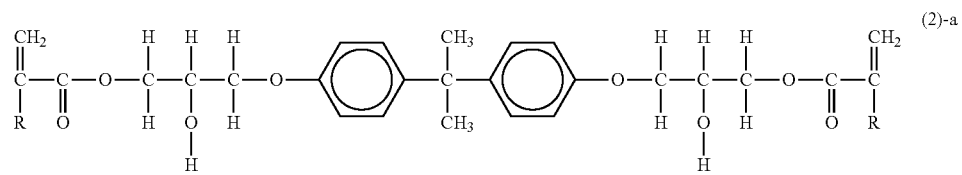

(2)-a wherein R is a hydrogen atom or a methyl group; and compounds represented by the following formula (3)-a:

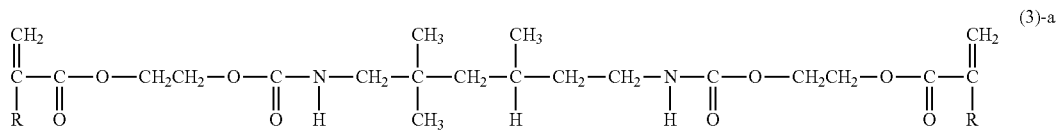

(3)-a wherein R is a hydrogen atom or a methyl group.

These (meth)acrylates can be used singly or in combination of two or more kinds.

Examples of the monomers having an acidic group include:
monomers having a carboxylic acid group or its anhydride group, such as (meth)acrylic acid and its anhydride, 1,4-di(meth)acryloxyethylpyromellitic acid, 6-(meth)acryloxyethylnaphthalene-1,2,6-tricarboxylic acid, N-(meth)acryloyl-p-aminobenzoic acid, N-(meth)acryloyl-o-aminobenzoic acid, N-(meth)acryloyl-m-aminobenzoic acid, N-(meth)acryloyl-5-aminosalicylic acid, N-(meth)acryloyl-4-aminosalicylic acid, 4-(meth)acryloxyethyltrimellitic acid and its anhydride, 4-(meth)acryloxybutyltrimellitic acid and its anhydride, 4-(meth)acryloxyhexyltrimellitic acid and its anhydride, 4-(meth)acryloxydecyltrimellitic acid and its anhydride, 2-(meth)acryloyloxybenzoic acid, 3-(meth)acryloyloxybenzoic acid, 4-(meth)acryloyloxybenzoic acid, β-(meth)acryloyloxyethyl hydrogensuccinate, β-(meth)acryloyloxyethyl hydrogenmaleate, β-(meth)acryloyloxyethyl hydrogenphthalate, 11-(meth)acryloyloxy-1,1-undecanedicarboxylic acid, and p-vinylbenzoic acid;
monomers having a phosphoric acid group, such as (2-(meth)acryloxyethyl)phosphoric acid, (2-(meth) acryloxyethylphenyl)phosphoric acid and 10-(meth) acryloxydecylphosphoric acid; and
monomers having a sulfonic acid group, such as p-styrenesulfonic acid and 2-acrylamido-2-methylpropanesulfonic acid.

Of these monomers having an acidic group, 4-methacryloxyethyltrimellitic acid and its anhydride are preferable.

These monomers having an acidic group can be used singly or in combination of two or more kinds. The monomers having an acidic group can be used as calcium salts. By the use of these monomers having an acidic group, the composition for hard tissue repair of the present invention tends to have more improved adhesion properties.

The monomer having an acidic group is preferably contained in an amount of 1 to 20 parts by weight, more preferably 1 to 10 parts by weight, still more preferably 1 to 8 parts by weight, based on 100 parts by weight of the total amount of the (meth)acrylate and the monomer having an acidic group contained in the composition for hard tissue repair of the present invention. If the amount thereof is out of the above range, an evil influence is sometimes exerted on the adhesive strength to hard tissues or the biocompatibility with organisms.

The amount of the monomer (A) is preferably in the range of 5 to 98.95 parts by weight, more preferably 17 to 98.5 parts by weight, still more preferably 24 to 84 parts by weight, based on 100 parts by weight of the total amount of the monomer (A), the later-described polymer (B) and the later-described polymerization initiator composition (C).

If the amount of the monomer (A) is less than the lower limit of the above range, viscosity is increased, and application or injection into bone tissues becomes difficult, that is, operability tends to be not excellent. If the amount of the monomer (A) exceeds the upper limit of the above range, adhesive strength and other properties, such as flexural elastic modulus, tensile strength, compression strength and flexural strength, tend to become poor.

In the composition for hard tissue repair of the present invention, at least one polymer (B) selected from acrylate polymers and methacrylate polymers is further contained (methacrylate polymers and acrylate polymers are sometimes generically referred to as "(meth)acrylate polymers" hereinafter).

Examples of the (meth)acrylate polymers include:
uncrosslinked polymers, such as polymethyl (meth)acrylate, polyethyl (meth)acrylate, a methyl (meth)acrylate/ethyl (meth)acrylate copolymer, a methyl (meth)acrylate/butyl (meth)acrylate copolymer and a methyl (meth)acrylate/styrene copolymer: and
crosslinked polymers, such as a methyl(meth)acrylate/ethylene glycol di(meth)acrylate copolymer, a methyl (meth)acrylate/triethylene glycol di(meth)acrylate copolymer and a copolymer of methyl (meth)acrylate and a butadiene-based monomer, and polymers which have partially formed calcium salts.

In the (meth)acrylate polymers, organic or inorganic composites in which metal oxides or metal salts are coated with the above-mentioned uncrosslinked polymers or crosslinked polymers are also included.

The weight-average molecular weight of the polymer is preferably in the range of 1,000 to 1,000,000, more preferably 50,000 to 500,000, still more preferably 100,000 to 500,000. The above molecular weight is a molecular weight in terms of standard polymethyl methacrylate, as determined by gel permeation chromatography (GPC).

The polymer (B) may be composed of polymer particles. When the polymer (B) is composed of polymer particles, they may be polymer particles of plural kinds.

Examples of such polymer particles include polymer particles (b1) having a weight-average molecular weight of $30 \times 10^4$ to $60 \times 10^4$ and a specific surface area of 1.5 to 4.5 $(m^2/g)$, polymer particles (b2) having a weight-average molecular weight of $5 \times 10^4$ to $20 \times 10^4$ and a specific surface area of 0.51 to 1.2 $(m^2/g)$, and polymer particles (b3) having a weight-average molecular weight of $5 \times 10^4$ to $20 \times 10^4$ and a specific surface area of 0.1 to 0.5 $(m^2/g)$.

The specific surface area of the polymer particles (b1) is preferably in the range of 1.5 to 4.5 $(m^2/g)$, more preferably 2.0 to 4.0 $(m^2/g)$.

The specific surface area of the polymer particles (b2) is preferably in the range of 0.51 to 1.2 $(m^2/g)$, more preferably 0.6 to 1.0 $(m^2/g)$.

The specific surface area of the polymer particles (b3) is preferably in the range of 0.1 to 0.5 $(m^2/g)$, more preferably 0.2 to 0.45 $(m^2/g)$.

The volume mean particle diameter of the polymer particles (b1) is usually in the range of 1 to 50 (μm), preferably 5 to 40 (μm). The volume mean particle diameter of the polymer particles (b2) is usually in the range of 0.1 to 40 (μm), preferably 1 to 20 (μm). The volume mean particle diameter of the polymer particles (b3) is usually in the range of 1 to 50 (μm), preferably 5 to 40 (μm).

When the polymer (B) is a polymer mixture composed of the polymer particles (b2) and the polymer particles (b3), and if necessary, the polymer particles (b1), the total amount of the polymer particles (b2) and the polymer particles (b3) is preferably not less than 2% by weight, more preferably not less than 5% by weight, based on the total weight of the polymer particles (b1), the polymer particles (b2) and the polymer particles (b3). The polymer mixture is sometimes composed of the polymer particles (b2) and the polymer particles (b3) in the total amount of 100% by weight.

When the total amount of the polymer particles (b2) and the polymer particles (b3) is not less than the lower limit of the above range, the polymer (B) is apt to be homogeneously dispersed in the monomer (A) and is more excellent in solubility in the monomer (A). Further, in the course of an operation of filling the composition in bones as bone cement or an operation of adhesion between hard tissues, between hard tissues and artificial substances, such as titanium and ceramic, or adhesion between hard tissues and other tissues such as soft tissues, rapid increase of viscosity can be inhibited and a sufficient operation time can be ensured. Furthermore, when the later-described X-ray contrast medium is added to the composition for hard tissue repair of the present invention, precipitation of the X-ray contrast medium does not take place during mixing, and the X-ray contrast medium can be homogeneously dispersed.

When the polymer particles (b1) are contained in the polymer particles, the total amount of the polymer particles (b2) and the polymer particles (b3) is preferably not more than 99% by weight, more preferably not more than 95% by weight, still more preferably not more than 90% by weight, based on the total weight of the polymer particles (b1), the polymer particles (b2) and the polymer particles (b3).

When the polymer particles (b1) are contained in the polymer particles, the content of the polymer particles (b1) is preferably not more than 98% by weight, more preferably not more than 95% by weight, based on the total weight of the polymer particles (b1), the polymer particles b2) and the polymer particles (b3). The content of the polymer (b1) is preferably not less than 1% by weight, more preferably not less than 5% by weight, still more preferably not less than 10% by weight, based on the total weight of the polymer particles (b1), the polymer particles (b2) and the polymer particles (b3). When the polymer particles (b1) are contained in the above amount in the polymer particles, precipitation of a contrast medium tends to rarely occur even if the composition of the present invention contains the contrast medium.

The amount of the (meth)acrylate polymer (B) is preferably in the range of 1 to 75 parts by weight, more preferably 1 to 73 parts by weight, still more preferably 15 to 73 parts by weight, based on 100 parts by weight of the total amount of the monomer (A), the (meth)acrylate polymer (B) and the later-described polymerization initiator composition (C).

If the amount of the (meth)acrylate polymer (B) is less than the lower limit of the above range, progress of polymerization becomes difficult, and adhesive strength and other properties, such as flexural elastic modulus, tensile strength, compression strength and flexural strength, tend to become poor. If the amount of the (meth)acrylate polymer (B) exceeds the upper limit of the above range, viscosity is increased, and application or use for bone tissues becomes difficult, that is, workability tends to be not excellent.

When the polymer (B) is a (meth)acrylate polymer and is a mixture of the polymer particles (b1), (b2) and (b3), the following embodiment is preferable under the conditions that the total amount of the polymer particles (b1), (b2) and (b3) is 100% by weight and the total amount of the polymer particles (b2) and (b3) is not less than 2% by weight, preferably not less than 5% by weight.

When the amount of the polymer (B) is not less than 35 parts by weight but less than 65 parts by weight based on 100 parts by weight of the total amount of the monomer (A), the polymer (B) and the polymerization initiator composition (C), the amount of the polymer particles (b1) is preferably in the range of 10% by weight to 98% by weight, more preferably 20% by weight to 95% by weight, the amount of the polymer particles (b2) is preferably not more than 90% by weight, more preferably not more than 80% by weight, and the amount of the polymer particles (b3) is preferably not more than 90% by weight, more preferably not more than 80% by weight.

The composition for hard tissue repair of the present invention is characterized by using the later-described organoboron compound (c1) as the initiator composition (C) contained, and when the organoboron compound is added to a composition containing a monomer, polymerization reaction begins in a relatively early stage and proceeds gently. This greatly differs from a case of using a peroxide as a polymerization initiator where a relatively long time is required for the beginning of polymerization even if the polymerization initiator is added, and if the polymerization reaction once begins, the reaction proceeds rapidly and is completed in a relatively short time. In order to prepare a composition that is preferably used for hard tissues, etc., therefore, it is important to use such a polymer (B) of the present invention in such an amount as described above based on the monomer (A). By the use of such a polymer (B), not only can workability be ensured over a long time but also fluidity and application properties that are preferable in use for hard tissues, etc. can be ensured.

The polymerization initiator composition (C) contained in the composition for hard tissue repair of the present invention contains an oragnoboron compound (c1) as an essential component, and can contain an aprotic solvent (c2) and an alcohol (c3), when needed. The organoboron compound (c1) has a feature that the polymerization rate is increased when a small amount of oxygen or water is present, and since the polymerization initiator composition (C) containing the organoboron compound (c1) is contained in the composition of the present invention, a part of the composition penetrates into a hard tissue to initiate polymerization at the contact interface when the composition comes into contact with an organism having moisture content as in an operation of filling in the hard tissue or application thereto. Hence, leakage of the monomer (A) and the composition is little. Further, even after the whole composition is cured in the organism, a residue of the monomer (A) tends to be smaller as compared with a composition using a peroxide as a polymerization initiator. Accordingly, the composition of the present invention is favorably used for organisms.

Examples of the organoboron compounds (c1) include trialkylboron, alkoxyalkylboron, dialkylborane and partially oxidized trialkylboron.

Examples of the trialkylborons include trialkylborons having an alkyl group of 2 to 8 carbon atoms, such as triethylboron, tripropylboron, triisopropylboron, tributylboron, tri-sec-butylboron, triisobutylboron, tripentylboron, trihexylboron, triheptylboron, trioctylboron, tricyclopentylboron and tricyclohexylboron. The alkyl group may be any of a straight-chain alkyl group, a branched alkyl group and a cycloalkyl group, and three alkyl groups contained in the trialkylboron may be the same or different.

The alkoxyalkylboron is, for example, monoalkoxydialkylboron or dialkoxymonoalkylboron. Specifically, the alkoxyalkylboron is, for example, monoalkoxydialkylboron such as butoxybutylboron. The alkyl group of the alkoxyalkylboron may be the same as or different from the alkyl part of the alkoxy group.

Examples of the dialkylboranes include dicyclohexylborane and diisoamylborane. Two alkyl groups of the dialkylborane may be the same or different. Two alkyl groups contained in the dialkylborane may be bonded to form a monocyclic structure or a bicyclo structure. Examples of such compounds include 9-borabicyclo[3.3.1]nonane.

The partially oxidized trialkylboron is a partially oxidized product of the above trialkylboron. As the partially oxidized trialkylboron, partially oxidized tributylboron is preferable. As the partially oxidized trialkylboron, partially oxidized trialkylboron obtained by the addition of oxygen in an amount of preferably 0.3 to 0.9 mol, more preferably 0.4 to 0.6 mol, based on 1 mol of the trialkylboron can be used.

Of the above organoboron compounds, tributylboron or partially oxidized tributylboron is preferable, and partially oxidized tributylboron is more preferable. When tributylboron or partially oxidized tributylboron is used as the organoboron compound (c1), not only is the operability of the composition improved but also the composition tends to have proper reactivity to organisms having moisture content. When tributylboron or partially oxidized tributylboron is used as the organoboron compound (c1), further, the reaction is initiated and proceeds even in a place of high moisture content such as an organism, so that the monomer rarely remains on the interface between the adhesive and the organism. Therefore, the injurious properties to the organism are extremely little. Such organoboron compounds (c1) can be used singly or in combination of two or more kinds.

In the polymerization initiator composition (C), an aprotic solvent (c2) may be further contained. Since the aprotic solvent is contained in the polymerization initiator composition (C) as above and the organoboron compound is diluted, exothermic properties of the organoboron compound (c1) having ignition properties become gentler to suppress ignition properties, and hence, handling of the composition during transportation, storage and mixing is facilitated. In the case where an extremely large amount of the composition of the present invention is used, rapid generation of heat can be inhibited because of proper lowering of the exothermic properties, and consequently, damage of an organism that is in contact with the composition of the present invention tends to be decreased. The boiling point of the aprotic solvent (c2) at 1 atm is usually in the range of 30° C. to 150° C., preferably 50° C. to 120° C. If the boiling point is lower than the lower limit of the above range, the aprotic solvent is evaporated or scattered from the polymerization initiator composition during transportation or storage, and the ignition suppressing effect of the organoboron compound (c1) tends to be lowered. If the boiling point exceeds the upper limit of the above range, a residue of the aprotic solvent in a cured product formed from the composition for hard tissue repair of the present invention is increased, and consequently, adhesion strength of the cured product to the affected part and other properties, such as flexural elastic modulus, tensile strength, compression strength and flexural strength, tend to become poor.

As the aprotic solvent (c2), a solvent that does not have a group containing active hydrogen, said group being reactive to the organoboron compound (c1), such as hydroxyl group or mercapto group, and is capable of forming a homogeneous solution together with the organoboron compound (c1) is preferable.

Examples of the aprotic solvents (c2) include:
hydrocarbons, such as pentane, hexane, cyclohexane, heptane, benzene and toluene;
halogenated hydrocarbons, such as fluorobenzene, 1,1-dichloroethane, 1,2-dichloroethane and so-called flons;
ethers, such as diethyl ether, diisopropyl ether, ethylene glycol dimethyl ether and tetrahydrofuran;
ketones, such as acetone, methyl ethyl ketone and diethyl ketone; and
esters, such as methyl acetate, ethyl acetate and isopropyl acetate.

Of these, saturated aliphatic hydrocarbons, such as pentane, hexane and heptane, ethers and esters are preferable, and hexane, diisopropyl ether and ethyl acetate are more preferable.

These aprotic solvents (c2) can be used singly or in combination of two or more kinds.

The content of the aprotic solvent (c2) in the polymerization initiator composition (C) is preferably in the range of 30 to 80 parts by weight based on 100 parts by weight of the organoboron compound (c1).

If the content of the aprotic solvent (c2) is less than the lower limit of the above range, satisfactory dilution effect is not obtained, and the effect to suppress generation of heat or ignition tends to be insufficient. On the other hand, if the content of the aprotic solvent (c2) exceeds the upper limit of the above range, polymerization initiation ability of the polymerization initiator composition (C) tends to be lowered.

In the polymerization initiator composition (C), an alcohol (c3) may be further contained in addition to the aprotic solvent (c2). By adding a small amount of the alcohol (c3) to the polymerization initiator composition (C), the reaction by the oragnoboron compound (c1) is made still gentler without lowering the polymerization activity, and even if the composition is brought into contact with paper or the like in air, burning or ignition tends to be suppressed.

The boiling point of the alcohol (c3) at 1 atm is usually in the range of 60° C. to 180° C., preferably 60° C. to 120° C. If the boiling point is lower than the lower limit of the above range, the alcohol is evaporated or scattered from the polymerization initiator composition during transportation or storage, and the ignition suppressing effect of the organoboron compound (c1) tends to be lowered. If the boiling point exceeds the upper limit of the above range, the curing time of the composition of the present invention tends to become longer, and adhesion strength of the cured product to the affected part and other properties, such as flexural elastic modulus, tensile strength, compression strength and flexural strength, tend to become poor.

Examples of the alcohols (c3) include methanol, ethanol, n-propanol and its isomers, n-butanol and its isomers, n-pentanol and its isomers, n-hexanol and its isomers, and n-heptanol and its isomers.

Of these alcohols (c3), alcohols of 4 or less carbon atoms, namely, methanol, ethanol, n-propanol and its isomers, and n-butanol and its isomers are preferable, and ethanol and n-propanol are more preferable.

These alcohols (c3) can be used singly or in combination of two or more kinds.

The content of the alcohol (c3) in the polymerization initiator composition (C) is usually in the range of 0.2 to 5 parts by weight, preferably 0.3 to 4.5 parts by weight, more preferably 0.5 to 4 parts by weight, based on 100 parts by weight of the organoboron compound (c1).

If the content of the alcohol (c3) is less than the lower limit of the above range, satisfactory dilution effect is not obtained, and the effect to suppress generation of heat or ignition tends to be insufficient. On the other hand, if the content of the alcohol (c3) exceeds the upper limit of the above range, polymerization initiation ability of the polymerization initiator composition (C) tends to become lower than needed.

When the alcohol (c3) and the aprotic solvent (c2) are used in combination, the content of the aprotic solvent (c2) in the polymerization initiator composition (C) is preferably in the range of 5 to 40 parts by weight, more preferably 10 to 30 parts by weight, still more preferably 10 to 25 parts by weight, based on 100 parts by weight of the organoboron compound (c1).

If the content of the aprotic solvent (c2) is less than the lower limit of the above range based on 100 parts by weight of the organoboron compound (c1), the effect to suppress generation of heat or ignition tends to be insufficient. On the other hand, if the content of the aprotic solvent (c2) exceeds the upper limit of the above range based on 100 parts by weight of the organoboron compound (c1), polymerization initiation ability of the polymerization initiator composition (C) tends to be lowered.

The amount of the polymerization initiator composition (C) is usually in the range of 0.05 to 20 parts by weight, preferably 0.5 to 10 parts by weight, more preferably 1 to 3 parts by weight, based on 100 parts by weight of the total amount of the monomer (A), the polymer (B) and the polymerization initiator composition (C).

If the amount of the polymerization initiator composition (C) is less than the lower limit of the above range, progress of polymerization is difficult, and the curing time tends to be prolonged. If the amount of the polymerization initiator composition (C) exceeds the upper limit of the above range, there is a possibility of lowering viscosity because of dilution or a possibility of exerting evil influence on safety. Moreover, it is presumed that rapid polymerization proceeds to form a polymerization product immediately.

In the composition for hard tissue repair, other components may be further contained when needed, as long as they do not exert evil influence on the performance of a hard tissue repair agent.

As one of the other components, a polymerization inhibitor (D) can be mentioned. Examples of the polymerization inhibitors (D) include hydroquinone compounds, such as hydroquinone and dibutylhydroquinone, hydroquinone monomethyl ether, phenols, such as 2,6-di-tert-butylphenol and 2,6-di-tert-butyl-p-cresol, catechol, pyrogallol, benzoquinone, 2-hydroxybenzoquinone, p-methoxyphenol, t-butylcatechol, butylated hydroxyanisole, butylated hydroxytoluene and t-butylhydroquinone. Of these, a mixture of hydroquinone monomethyl ether and 2,6-di-tert-butyl-p-cresol is preferably used.

Of these polymerization inhibitors (D), hydroquinone monomethyl ether is sometimes preferable from the viewpoint of good stability of the hydroquinone monomethyl ether itself.

The above polymerization inhibitors (D) can be used singly or in combination of two or more kinds.

When the polymerization inhibitor (D) is added, the amount thereof is preferably in the range of 10 to 5000 ppm, more preferably 50 to 1000 ppm, still more preferably 50 to 500 ppm, based on the whole amount of the composition for hard tissue repair.

It is also preferable to add the polymerization inhibitor (D) in an amount of 10 to 5000 ppm based on the monomer (A).

By preparing such a composition, for example, when the composition is applied to a part, such as the affected part (hard tissue containing moisture such as body fluid) in the surgical operation, the composition becomes more excellent in ensuring application properties and a proper curing time and can be more stably handled than before. Moreover, the composition is excellent in workability.

Although the amount of the polymerization inhibitor (D) is as described above, the polymerization inhibitor (D) is more preferably added in an amount of 50 to 1000 ppm, still more preferably 50 to 500 ppm, based on the monomer (A). By preparing such a composition, for example, the composition can be not only handled stably during application but also cured efficiently after application. If the content of the polymerization inhibitor (D) is less than the lower limit of the above range, curing takes place immediately after mixing of the monomer (A), the polymer (B) and the polymerization initiator composition (C), and hence, application tends to become difficult. On the other hand, if the content of the polymerization inhibitor (D) exceeds the upper limit of the above range, polymerization initiation ability of the polymerization initiator composition (C) is lowered, and the curing time becomes longer than needed. Hence, medical use of the composition tends to become difficult.

As one of the other components, an ultraviolet light absorber can be further mentioned. Examples of the ultraviolet light absorbers include:

benzotriazole compounds, such as 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis($\alpha,\alpha$-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, a mixture of 2-(3'-tert-butyl-2'-hydroxy-5'-(2-isooctyloxycarbonylethyl)phenyl)benzotriazole and 2,2'-methylene-bis[4-(1,1,3,3-tetramethylbutyl)-6-benzotriazol-2-ylphenol], an ester interchange reaction product of 2-[3'-tert-butyl-5'-(2-methoxycarbonylethyl)-2'-hydroxyphenyl]benzotriazole with polyethylene glycol 300, and [[R—CH$_2$CH$_2$—COOCH$_2$]$_3$]$_2$— (wherein R is 3'-tert-butyl-4'-hydroxy-5'-2H-benzotriazol-2-ylphenyl);

benzophenone compounds, such as 2,4-dihydroxybenzophenone, 2-hydroxy-4-methoxybenzophenone, 2-hydroxy-4-octoxybenzophenone, 2-hydroxy-4-decyloxybenzophenone, 2-hydroxy-4-dodecyloxybenzophenone, 2-hydroxy-4-benzyloxybenzophenone, 2,2',4,4'-tetrahydroxybenzophenone, and 2,2'-dihydroxy-4,4'-dimethoxybenzophenone;

4-tert-butylphenylsalicylate, phenylsalicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hyderoxybenzoate, hexadecyl 3,5-di-tert-butyl-4-hyderoxybenzoate, octadecyl 3,5-di-tert-butyl-4-hyderoxybenzoate, 2-methyl-4,6-di-tert-butylphenyl benzoate, and 3,5-di-tert-butyl-4-hydroxybenzyl benzoate;

hindered amine compounds, such as bis(2,2,6,6-tetramethylpiperidyl)sebacate, bis(2,2,6,6-tetramethylpiperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, a condensation product of 1-hydroxyethyl-2,2,6,6-tetramethyl-4-hydroxypiperidine and succinic acid, a condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethyl-4-piperidyl)-2-n-butyl-2-(2-hydroxy-3,5-di-tertbutylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, a condensation product of N,N'-bis(2,2,6,6-tetramethyl-4-piperidyl) hexamethylenediamine and 4-morpholino-2,6-dichloro-1,3,5-triazine, a condensation product of 2-chloro-4,6-di-(4-n-butylamino-2,2,6,6-tetramethylpiperidyl)-1,3,5-triazine and 1,2-bis(3-aminopropylamino)ethane, a condensation product of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, and 3-dodecyl-1-(1,2,2,6,6-pentamethyl-4-piperidyl)pyrrolidine-2,5-dione;

oxalamide compounds, such as 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, a mixture of 2-ethoxy-5-tert-butyl-2'-ethyloxanilide and 2-ethoxy-2'-ethyl-5,4'-di-tert-butyloxanilide, a mixture of o-methoxy- and p-methoxy-di-substituted oxanilides, and a mixture of o-ethoxy- and p-ethoxy-di-substituted oxanilides;

2-(2-hydroxyphenyl)-1,3,5-triazine compounds, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-tri azine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, and 2-[4-dodecyl/tridecyloxy-(2-hydroxypropyl)oxy-2-hydroxyphenyl]-4,6-bis(2,4-dimethylphenyl)-1,3,5-triazine; and phosphite compounds or phosphonite compounds, such as triphenyl phosphite, diphenylalkyl phosphite, phenyldialkyl phosphite, tris(nonylphenylphosphite), trilauryl phosphite, trioctadecyl phosphite, distearyl pentaerythrytyl diphosphite, tris(2,4-di-tert-butylphenyl)phosphite, diisodecyl pentaerythrityl diphosphite, bis(2,4-di-tert-butylphenyl)pentaerythrityl diphosphite, bis(2,6-di-tert-butyl-4-methylphenyl) pentaerythrityldiphosphite, bisisodecyloxypentaerythrityl diphosphite, bis(2,4-di-tert-butyl-6-methylphenyl)pentaerythrityldiphosphite, bis(2,4,6-tri-tert-butylphenyl)pentaerythrityl diphosphite, tristearyl sorbityl triphosphite, tetrakis(2,4-di-tert-butylphenyl)-4,4'-biphenylenediphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocine, bis(2,4-di-tert-butyl-6-methylphenyl)methyl phosphite, and bis(2,4-di-tert-butyl-6-methylphenyl) ethyl phosphite.

As the ultraviolet light absorber, a benzotriazole compound is preferable.

When the ultraviolet light absorber is added, the amount thereof is preferably in the range of 10 to 1,000 ppm, more preferably 100 to 800 ppm, based on the monomer (A). By adding the ultraviolet light absorber as above, coloring of a liquid containing a monomer is suppressed, and storage stability of the monomer itself tends to be enhanced.

As examples of the other components, a flexibilizer and a plasticizer can be further mentioned.

Examples of the flexibilizers include rubbers, such as natural rubbers and synthetic rubbers, and elastomers, such as thermoplastic elastomers. By the use of such a flexibilizer, flexibility of the composition for hard tissue repair can be enhanced.

Examples of the synthetic rubbers include EPT (ethylene/propylene/terpolymer). Examples of the thermoplastic elastomers include styrene-based elastomers, vinyl chloride-based elastomers, olefin-based elastomers, polyester-based elastomers, polyamide-based elastomers, and urethane-based elastomers.

The molecular weight of the elastomer is usually in the range of 1,000 to 1,000,000, preferably 2,000 to 500,000. The glass transition point (Tg) of the elastomer is usually not higher than 20° C., preferably not higher than 0° C.

Examples of the plasticizers include hydroxycarboxylic acid esters, such as citrate esters, isocitrate esters, tartrate esters, malate esters, lactate esters, glycerate esters and glycolate esters; trimethyl trimellitate, diethylene glycol dibenzoate, diethyl malonate, triethyl o-acetylcitrate, benzyl butyl phthalate, dipropylene glycol dibenzoate, diethyl adipate, tributyl o-acetylcitrate, dimethyl sebacate, and alkylene glycol diester.

Although the amount of the flexibilizer and the plasticizer is properly selected according to the types of the materials, they are used so that they may be usually contained in an amount of 0 to 30% by weight, preferably 0 to 20% by weight, more preferably 0 to 10% by weight, in the whole composition for hard tissue repair.

As one of the other components, a preservative can be further mentioned.

Examples of the preservatives include:
methylparaben, methylparaben sodium, ethylparaben, propylparaben, propylbaraben sodium, butylparaben;
cresol, chlorocresol;
resorcinol, 4-n-hexylresorcinol, 3a,4,7,7a-tetrahydro-2-((trichloromethyl)thio)-1H-isoindole-1,3(2H)dione;
benzalkonium chloride, benzalkonium sodium chloride, benzethonium chloride;
benzoic acid, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercuric compounds, such as phenylmercuric borate, phenylmercuric nitrate and phenylmercuric acetate, and formaldehyde.

As examples of the other components, there can be further mentioned anti-infectious agents, antibiotics, antibacterial agents, anti-virus agents, analgesics, compositions of analgesics, anorectic drugs, antihelmintic drugs, antiarthritic agents, antiasthmatic drugs, anticonvulsants, antidepressants, antidiuretics, antidiarrheal agents, antihistamine drugs, anti-inflammatory drugs, antimigraine drugs, antiemetic agents, antineoplastic drugs, antiparkinsonian agents, antipruritic drugs, antipsychotics, antipyretic drugs, antispasmodic drugs, anticholinergic agents, sympathomimetic agents, cardiovascular drugs, antiarrhythmic drugs, antihypertensive drugs, diuretics, vasodilators, immunosuppressant drugs, muscle-relaxant drugs, parasympatholytic drugs, stimulants, sedative drugs, tranquilizers, cholinergic agents, chemotherapeutic drugs, radio pharmaceuticals, bone inductive drugs, heparin neutralizer agents of static bladder, procoagulants, hemostatic agents, xanthine derivatives, hormones, proteins of natural origin or proteins synthesized by genetic engineering, polysaccharides, glycoproteins, lipoproteins, oligonucleotides, antibody, antigen, vasopressin, vasopressin analogs, epinephrine, selectin, clot promoting toxicants, plasminogen activating factor inhibitors, platelet activators, bone-forming factors, and synthetic peptides having hemostatic action. Since these components are contained, the composition of the present invention can be used also for the drug delivery system or the purpose of regenerative medicine.

Examples of the antibacterial agents include:
element iodine, solid polyvinylpyrrolidone iodine, polyvinylpyrrolidone iodine;
phenol compounds, such as tribromophenol, trichlorophenol, tetrachlorophenol, nitrophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 2,4-dichloro-3,5-dimethylphenol, 4-chlorothymol, chlorophene, triclosan, fenticlor, phenol, 2-methylphenol, 3-methylphenol, 4-methylphenol, 4-ethylphenol, 2,4-dimethylphenol, 2,5-dimethylphenol, 3,4-dimethylphenol, 2,6-dimethylphenol, 4-n-proylphenol, 4-n-butylphenol, 4-n-aminophenol, 4-tert-amylphenol, 4-n-hexylphenol, 4-n-heptylphenol, monoalkylhalophenol, polyalkylhalophenol, aromatic halophenol, and ammonium salts, alkali metal salts and alkaline earth metal salts of these substances;
silver nitrate, hexachlorophene, merbromin, tetracycline-.HCl, tetracycline hydrate and erythromycin.

In the composition for hard tissue repair, bone-forming factor, etc. may be contained for the purpose of accelerating tissue reparation and the like.

As examples of the other components, there can be further mentioned perfumes, such as orange oil, grapefruit oil, lemon oil, lime oil, clove oil, wintergreen oil, peppermint oil, peppermint spirit, banana distillate, cucumber distillate, honey distillate, rose water, menthol, anethole, alkyl salicylate, benzaldehyde, monosodium glutamate, ethylvanillin, thymol and vanillin.

Furthermore, an inorganic filler, an organic filler, an organic composite filler, a filler colorant, etc. may be contained as the other components to impart X-ray contrast property and to enhance properties such as adhesive strength and compression strength.

Examples of the inorganic fillers include:
metal oxide powders, such as zirconium oxide, bismuth oxide, titanium oxide, zinc oxide and aluminum oxide particles;
metal salt powders, such as bismuth carbonate, zirconium phosphate and barium sulfate;
glass fillers, such as silica glass, aluminum-containing glass, barium-containing glass, strontium-containing glass and zirconium silicate glass;
fillers having silver sustained-release property;
fillers having calcium sustained-release property; and
fillers having fluorine sustained-release property.

From the viewpoint of formation of strong bonding between an inorganic filler and the monomer (A) after curing, it is preferable to use an inorganic filler having been subjected to surface treatment such as silane treatment or polymer coating.

These inorganic fillers can be used singly or in combination of two or more kinds.

As one of the other components, an X-ray contrast medium can be mentioned. Examples of the X-ray contrast media include zirconium oxide, barium sulfate, bismuth carbonate, calcium tungstate, ytterbium and an iodine compound. Of these X-ray contrast media, zirconium oxide is preferable from the viewpoint that zirconium oxide has actual results of use for hard tissues, particularly as bone cement, and it exhibits higher X-ray contrast property and higher dispersibility as compared with barium sulfate that also has actual results of use.

Although the amount of the X-ray contrast medium is properly selected according to the use purpose, etc., it is usually in the range of 10 to 70 parts by weight, preferably 15 to 65 parts by weight, based on 100 parts by weight of the whole weight of the composition for hard tissue repair excluding the X-ray contrast medium.

The composition for hard tissue repair of the present invention is excellent in operability as a hard tissue repair agent, that is, application properties and injection properties.

In the present invention, the monomer (A), the (meth) acrylate polymer (B), the polymerization initiator composition (C) and the components to be contained when needed are previously mixed to prepare a composition for hard tissue repair, and the composition can be used by applying it to the affected part. The temperature of heat generated by the composition prepared as above is usually not higher than 70° C., and the risk of doing damage to the affected tissue becomes lower.

When these components are mixed, the order of mixing is not specifically restricted, but it is preferable that the monomer (A) is first mixed with the polymerization initiator composition (C) and subsequently mixed with the polymer (B), from the viewpoint that the stability of the resulting composition for hard tissue repair is more excellent.

When the composition for hard tissue repair of the present invention contains the polymerization inhibitor (D), it is preferable that a mixture of the monomer (A) and the polymerization inhibitor (D) is first mixed with the polymerization initiator composition (C) and subsequently mixed with the polymer (B), from the viewpoint that the stability of the resulting composition is more excellent.

A cured product, which is obtained from the composition for hard tissue repair, is given 24 hours after the preparation of the composition and has a thickness of not less than 0.1 µm, a length of not less than 25 mm and a width of not less than 2 mm, preferably has a flexural elastic modulus, as measured under the conditions of a test rate of 2 mm/min, of not less than 100 MPa, and preferably has a tensile strength, as measured under the conditions of a test rate of 1 mm/min, of not less than 10 MPa, and preferably has a flexural strength, as measured under the conditions of a test rate of 2 mm/min, of not less than 10 MPa.

The flexural elastic modulus of the above cured product may be preferably not less than 100 MPa, more preferably not less than 150 MPa, still more preferably not less than 200 MPa.

When the composition for hard tissue repair contains an X-ray contrast medium, a cured product, which is obtained from the composition for hard tissue repair, is given 24 hours after the preparation of the composition and has a thickness of 0.5 mm, a length of 25 mm and a width of 2 mm, preferably has a flexural elastic modulus, as measured under the conditions of a test rate of 2 mm/min, of not less than 1800 MPa, more preferably not less than 2000 MPa, still more preferably not less than 2200 MPa, and preferably has a flexural strength, as measured under the conditions of a test rate of 2 mm/min, of not less than 50 MPa.

Further, a cured product, which is obtained from the composition for hard tissue repair and is given 24 hours after the preparation of the composition, preferably has a shear strength of not less than 10 MPa (test rate: 2 mm/min). Furthermore, this cured product preferably has a compression strength of not less than 10 MPa (test rate: 2 mm/min). When the composition for hard tissue repair contains an X-ray contrast medium, a cured product, which is obtained from the composition for hard tissue repair, is given 24 hours after the preparation of the composition and has a thickness of 5 mm, a length of 10 mm and a width of 10 mm, preferably has a compression strength, as measured under the conditions of a test rate of 2 mm/min, of not less than 70 MPa, more preferably not less than 75 MPa.

The composition for hard tissue repair is excellent in adhesion between hard tissues, filling in hard tissues, adhesion between hard tissues and artificial substances, such as titanium, ceramics and stainless steel, adhesion between hard tissues and other tissues such as soft tissues, etc., excluding dental applications.

A film, which is obtained from the composition for hard tissue repair of the present invention, is given 24 hours after the preparation of the composition and has a thickness of not less than 1 μm (preferably not more than 1 cm), a length of not less than 25 mm and a width of not less than 2 mm, may preferably have a tensile elongation, as measured under the conditions of a test rate of 1 mm/min, of not less than 30%, more preferably not less than 40%, still more preferably not less than 50%.

When the composition for hard tissue repair contains an X-ray contrast medium, a cured product, which is obtained from the composition for hard tissue repair, is given 24 hours after the preparation of the composition and has a thickness of 0.5 mm, a length of 25 mm and a width of 2 mm, preferably has a tensile strength, as measured under the conditions of a test rate of 1 mm/min, of not less than 30 MPa, more preferably not less than 31 MPa.

Accordingly, the composition of the present invention is favorable for hard tissue repair.

The composition for hard tissue repair of the present invention preferably has a viscosity of 0.4 to 2,000,000 cp within 30 seconds after mixing of the components (A), (B) and (C) and the components to be contained when needed.

Since the viscosity is in the above range, the composition is excellent in operability, that is, for example, application of the composition in the hard tissue repair is easily made, or injection of the composition to fill it in bone tissue is easily made.

From the viewpoints of operability and fluidity, the viscosity is preferably in the range of 0.4 to 500,000 cp, more preferably 1 to 500,000 cp.

The composition for hard tissue repair of the present invention preferably has a viscosity of 1 to 2,000,000 cp, more preferably 10 to 2,000,000 cp, 60 seconds after mixing of the components (A), (B) and (C) and the components to be contained when needed.

Further, the composition for hard tissue repair of the present invention preferably has a viscosity of 10 to 80,000,000 cp, more preferably 50 to 50,000,000 cp, still more preferably 100 to 20,000,000 cp, 540 seconds after mixing of the components (A), (B) and (C) and the components to be contained when needed.

Since the viscosity is in the above range, the composition is excellent in operability, that is, for example, application of the composition in the hard tissue repair is easily made, or transfusion of the composition into a cement gun to fill it in bone tissue or injection of the composition into bone is easily made.

Prior to or during curing of the composition for hard tissue repair of the present invention, the composition may be irradiated with electromagnetic waves, such as visible light, ionizing radiation (e.g., γ-rays) or electron rays, to perform sterilization. Irradiation with visible light is sometimes desirable because the visible light does not greatly change the curing conditions. Sterilization may be carried out by treatment with gas, such as dry heat, steam, ethylene oxide (EO) or hydrogen peroxide, filtration, treatment with liquid, autoclave sterilization, or the like.

Prior to application of the composition for hard tissue repair of the present invention to the affected part, the surface of the affected part may be disinfected with a disinfectant such as alcohol.

Prior to application of the composition for hard tissue repair of the present invention to the affected part, pretreatment may be further carried out for the purpose of improving adhesion to the affected part. The pretreatment liquid is, for example, an aqueous solution containing 1 to 15% by weight of citric acid and 1 to 5% by weight of iron(III) chloride.

If there is a fear that the form or the performance of the composition for hard tissue repair of the present invention varies over a long time, thereby impairing the effect of the present invention, it is possible that all the components, which consist of the monomer (A), the (meth)acrylate polymer (B), the polymerization initiator composition (C) and the components to be contained when needed and are used for hard tissue repair, are stored in the form of a kit for hard tissue repair having two or more members in which the above components are encased independently or in groups divided in an optional combination, and prior to use, the components are mixed to form the composition for hard tissue repair. The members for encasing the components therein are, for example, sealable resin containers having gas barrier properties in order to prevent evaporation or scattering of the monomer (A) and the polymerization initiator composition (C), or glass syringes. The members for encasing the polymer (B) therein are, for example, resin containers having good sealing properties in order to prevent moisture absorption, or glass containers. As for the quantity to be encased, there is a case where the quantity that is used up one time is encased or a case where the quantity that is used plural times is encased.

Examples of manners to store the components include a manner in which the components are divided into three groups consisting of a mixture of the component (A) and the components to be contained when needed, a mixture of the component (B) and the components to be contained when needed, and a mixture of the component (C) and the components to be contained when needed, followed by storing them; a manner in which the components are divided into two groups consisting of a mixture of the component (A), the component (B) and the components to be contained when needed, and the component (C), followed by storing them; a manner in which the components are divided into two groups consisting of a mixture of the component (A) and the component (B), and a mixture of the component (C) and the components to be contained when needed, followed by storing them; a manner in which the components are divided into two groups consisting of a mixture of the component (A), the component (B) and a part of the components to be contained when needed, and a mixture of the component (C) and a residue of the components to be contained when needed, followed by storing them; a manner in which the components are divided into two groups consisting of a mixture of the component (A) and the components to be contained when needed, and a mixture of the component (B) and the component (C), followed by storing them; a manner in which the components are divided into two groups consisting of the component (A), and a mixture of the component (B), the component (C) and the components to be contained when needed, followed by storing them; and a manner in which the components are divided into two groups consisting of a mixture of the component (A) and apart of the components to be contained when needed, and a mixture of the component (B), the component (C) and a residue of the components to be contained when needed, followed by storing them.

When the polymerization inhibitor (D) is contained, examples of manners to store the components include a manner in which the components are divided into three groups consisting of a mixture of the component (A) and the components to be contained when needed, a mixture of the component (B) and the components to be contained when needed, and a mixture of the component (C) and the components to be contained when needed, followed by storing them; a manner in which the components are divided into two groups consisting of a mixture of the component (A), the component (B), the component (D) and the components to be contained when needed, and the component (C), followed by storing them; a manner in which the components are divided into two groups consisting of a mixture of the component (A), the component (B) and the component (D), and a mixture of the component (C) and the components to be contained when needed, followed by storing them; a manner in which the components are divided into two groups consisting of a mixture of the component (A), the component (B), the component (D) and a part of the components to be contained when needed, and a mixture of the component (C) and a residue of the components to be contained when needed, followed by storing them; a manner in which the components are divided into two groups consisting of a mixture of the component (A), the component (D) and the components to be contained when needed, and a mixture of the component (B) and the component (C), followed by storing them; a manner in which the components are divided into two groups consisting of a mixture of the component (A) and the component (D), and a mixture of the component (B), the component (C) and the components to be contained when needed, followed by storing them; and a manner in which the components are divided into two groups consisting of a mixture of the component (A), the component (D) and a part of the components to be contained when needed, and a mixture of the component (B), the component (C) and a residue of the components to be contained when needed, followed by storing them.

When a mixture of a monomer having an acidic group and a monomer having no acidic group is used as the monomer (A), the components may be stored in such a manner that the monomer having an acidic group is not in contact with the polymerization initiator composition, in addition to the above manners. Examples of such manners include a manner in which the components are divided into two groups consisting of a mixture of the monomer having an acidic group, the component (B) and the components to be contained when needed, and a mixture of the monomer having no acidic group and the component (C), followed by storing them; a manner in which the components are divided into two groups consisting of a mixture of the monomer having an acidic group and the component (B), and a mixture of the monomer having no acidic group, the component (C) and the components to be contained when needed, followed by storing them; a manner in which the components are divided into two groups consisting of a mixture of the monomer having an acidic group and the components to be contained when needed, and a mixture of the monomer having no acidic group, the component (B) and the component (C), followed by storing them; and a manner in which the components are divided into two groups consisting of the monomer having an acidic group, and a mixture of the monomer having no acidic group, the component (B), the component (C) and the components to be contained when needed, followed by storing them.

The components divided into two groups are placed in separate members, e.g., containers such as syringes, then the members are encased in a kit for hard tissue repair, and the kit can be provided as an article.

The constitution of the kit for hard tissue repair is not specifically restricted as long as there is no fear that the form or the performance is changed by the storage to impair the effect of the present invention, but the kit preferably has constitution in which the monomer (A), the polymer (B) and the polymerization initiator composition (C) are each independently encased, and the monomer (A) is first mixed with the polymerization initiator composition (C) containing an organoboron compound and subsequently mixed with the polymer (B). By virtue of such constitution, a composition for hard tissue repair having more stable performance tends to be obtained.

Examples of the kits for hard tissue repair include:
a kit having members (e.g., containers, syringes) in which the monomer (A), the polymer (B) and the polymerization initiator composition (C) are each independently encased and having a member (e.g., mixing container, mixing dish) for taking out the encased components from the members and mixing them; and
a kit having one container which has three or more chambers separated by partitions, in said chambers the monomer (A), the polymer (B) and the polymerization initiator composition (C) being each independently encased, and having a stirring unit for mixing the monomer (A) and the polymerization initiator composition (C) with the polymer (B), said components (A) and (C) having passed through a bypass formed in a syringe owing to rapture of the partitions or shifting of the partitions.

When the kit contains the polymerization inhibitor (D), the kit preferably has constitution in which a mixture containing the monomer (A) and the polymerization inhibitor (D), the polymer (B) and the polymerization initiator composition (C) are each independently encased, and the mixture containing the monomer (A) and the polymerization inhibitor (D) is first mixed with the polymerization initiator composition (C) containing an organoboron compound and subsequently mixed with the polymer (B). By virtue of such constitution, a composition having more stable performance tends to be obtained.

Examples of such kits include:
a kit having members (e.g., containers, syringes) in which a mixture containing the monomer (A) and the polymerization inhibitor (D), the polymer (B) and the polymerization initiator composition (C) are each independently encased and having a member (e.g., mixing container, mixing dish) for taking out the encased components from the members and mixing them; and
a kit having one container which has three or more chambers separated by partitions, in said chambers a mixture containing the monomer (A) and the polymerization inhibitor (D), the polymer (B) and the polymerization initiator composition (C) being each independently encased, and having a stirring unit for mixing the mixture containing the monomer (A) and the polymerization inhibitor (D) and the polymerization initiator composition (C) with the polymer (B), said mixture and said component (C) having passed through a bypass formed in a syringe owing to rapture of the partitions or shifting of the partitions.

The kit having one container wherein the components are encased in the separated three or more chambers requires less labor as compared with a means wherein the composition of the present invention is divided, placed in two or more members, typically containers, and mixed immediately before use. Moreover, this kit uses no mixing container or the like and can be economically used by taking a necessary amount of the composition out of the container and bringing it into contact with a jig such as sponge.

It is also possible that a jig that is used for applying the composition for hard tissue repair to the affected part, e.g., hard tissue such as bone or cartilage, soft tissue, or an artificial substance such as titanium, ceramic or stainless steel is allowed to contain apart or the whole of the polymerization initiator composition (C) in advance, and the jig is brought into contact with the monomer (A) or a mixture containing the monomer (A) and the polymerization inhibitor (D), the polymer (B) and the components to be contained when needed to prepare the composition for hard tissue repair of the present invention in situ, followed by applying it to the affected part.

Examples of the jigs for applying the composition to the affected part include a brush, a fiber ball, a cloth, a sponge ball and a piece of sponge.

In the kit for hard tissue repair or the like, the aforesaid disinfectant liquid such as alcohol, the aforesaid pretreatment solution for improving adhesion properties, etc. may be included.

When the components of the composition are stored in the kit or the like, they may be subjected to sterilization treatment with electromagnetic waves such as visible light preferably under the conditions that the components are not modified (e.g., monomer is not cured).

The composition for hard tissue repair of the present invention can be used as bond cement that is used for adhesion between hard tissues, filling in hard tissues, adhesion between hard tissues and artificial substances, such as titanium, ceramics and stainless steel, adhesion between hard tissues and other tissues such as soft tissues, fixation of hard tissues, such as bone and cartilage, to artificial joints, etc., or can be used as a filling material into bone defectives, a bone substitute material, an artificial bone or the like.

EXAMPLES

The present invention is further described with reference to the following examples, but it should be construed that the present invention is in no way limited to those examples.

Examples 1A to 10A, Comparative Examples 1A and 2A

Reagents

In the examples, the following compounds and composition were used as the monomer (A), the polymer (B) and the polymerization initiator composition (C).

Monomer (A): 4-META/MMA, methyl methacrylate solution of 4-methacryloxyethyltrimellitic anhydride (weight ratio: about 5%)

Polymer (B): mixture of three kinds of the following PMMA (polymethyl methacrylates) (b1) to (b3) and pigment The weight ratios of these components are as follows: in 100 parts by weight of the total amount of the three kinds of PMMA and the pigment, (b1) is contained in an amount of 20.03 parts by weight, (b2) is contained in an amount of 62.5 parts by weight, (b3) is contained in an amount of 12.5 parts by weight, and the pigment is contained in the residual amount.

Molecular weights and properties of the PMMA (b1) to (b3) are as follows.

(b1) weight-average molecular weight: 450,000, volume mean particle diameter: 26.7 μm, specific surface area: 2.913 m$^2$/g (b2) weight-average molecular weight: 140,000, volume mean particle diameter: 8.2 μm, specific surface area: 0.827 m$^2$/g (b3) weight-average molecular weight: 140,000, volume mean particle diameter: 24.6 μm, specific surface area: 0.371 m$^2$/g The volume mean particle diameter of PMMA (refractive index: 1.49) was measured in the following manner. As a dispersion medium, special grade reagent methanol (refractive index: 1.33, available from Wako Pure Chemical Industries, Ltd.) was used. The PMMA was dispersed in the dispersion medium by an ultrasonic homogenizer integrated in the apparatus for 5 minutes (output: 25 W), and the measurement was carried out under the concentration conditions of the proper range of the apparatus Loading Index at a circulation rate of 50% (100%:65 ml/sec) by the use of Microtrac MT3300EXII (particle size distribution meter manufactured by Microtrac Inc.). The specific surface area is a value determined by nitrogen gas adsorption at the liquid nitrogen temperature (77 K) using Autosorb 3 (manufactured by Quantachrome Instruments), and is a value measured by BET method.

Polymerization initiator composition (C): TBB A type, namely, partially oxidized tributylboron: 80 parts by weight, hexane: 19 parts by weight, ethanol: 1 part by weight Evaluation of Viscosity In a sample tube, the polymer (B) was weighed in accordance with a blending ratio described in Examples 1A to 6A and Comparative Example 1A of the following Table 1. In the sample tube in which the polymer (B) had been weighed, the monomer (A) and the polymerization initiator composition (C), which had been mixed together in a different sample tube in accordance with a blending ratio described in Examples 1A to 6A and Comparative Example 1A of the following Table 1 similarly to the above, were injected, and they were mixed together at 25° C. to prepare an adhesive composition of the present invention. Within 30 seconds after the preparation, viscosity of the composition was measured. The viscosity at the time of preparation was not less than 0.4 cp, and it was confirmed that the viscosity increased with time. The viscosity was measured by an E type viscometer (manufactured by Tokyo Keiki Inc., EHP type) at 25° C. The evaluation results are set forth in Table 1.

Evaluation of Application Properties

In a syringe having a cap at the luer part, the polymer (B) was weighed in accordance with a blending ratio described in Examples 1A to 6A and Comparative Example 1A of the following Table 1. In this syringe, the monomer (A) and the polymerization initiator composition (C), which had been mixed together in a sample tube in accordance with a blending ratio described in Examples 1A to 6A and Comparative Example 1A of the following Table 1 similarly to the above, were injected, and they were mixed together at 25° C. Thereafter, the cap of the syringe was removed, then a nozzle having a width of 1 cm and a thickness of 1 mm was fitted, and 1 ml of the composition mixed was applied by 4 cm onto a polyethylene sheet. The application properties were evaluated based on the 5-grade evaluation of 1 to 5. That is to say, a case where the width of the applied composition was not less than 1 cm but less than 1.2 cm was evaluated to be 5; a case where the width of the applied composition was not less than 1.2 cm but less than 1.4 cm was evaluated to be 4; a case where the width of the applied composition was not less than 1.4 cm but less than 1.6 cm was evaluated to be 3; a case where the width of the applied composition was not less than 1.6 cm was evaluated to be 2; and a case where application was impossible was evaluated to be 1. The evaluation results are set forth in Table 1.

Evaluation of Extrusion from Container

In a syringe whose discharge opening had been closed with a cap, the polymer (B) was weighed in accordance with a blending ratio described in Examples 1A to 6A and Comparative Example 1A of the following Table 1. In the syringe in which the polymer (B) had been placed, the monomer (A) and the polymerization initiator composition (C), which had been mixed together in a sample tube in accordance with a blending ratio described in Examples 1A to 6A and Comparative Example 1 of the following Table 1 similarly to the above, were injected, and they were mixed together at 25° C. Thereafter, the cap of the syringe in which the three components of (A), (B) and (C) had been placed was removed, then a needle of 11G was fitted, and 1 ml of the composition mixed was extruded onto a polyethylene sheet. The extrusion was evaluated based on the 3-grade evaluation of 1 to 3. That is to say, a case where the whole amount of the composition was extruded within 20 seconds at a pressure of 50 kPa was evaluated to be 3; a case where the whole amount of the composition was extruded in not shorter than 20 seconds but shorter than 60 seconds was evaluated to be 2; and a case where the whole amount of the composition was not extruded even in not shorter than 60 seconds was evaluated to be 1. The evaluation results are set forth in Table 1.

TABLE 1

| | Adhesive composition (part(s) by weight) | Viscosity 30 seconds after mixing (cp) | Application properties | Extrusion from container |
|---|---|---|---|---|
| Ex. 1A | Monomer (A): 1680 mg (87.2)<br>Polymer (B): 192.7 mg (10.0)<br>Polymerization initiator composition (C): 54 mg (2.8) | 0.5 | 2 | 3 |
| Ex. 2A | Monomer (A): 1680 mg (82.4)<br>Polymer (B): 192.7 mg (15.0)<br>Polymerization initiator composition (C): 54 mg (2.6) | 1 | 4 | 3 |
| Ex. 3A | Monomer (A): 1680 mg (77.5)<br>Polymer (B): 433.5 mg (20.0)<br>Polymerization initiator composition (C): 54 mg (2.5) | 24 | 4 | 3 |
| Ex. 4A | Monomer (A): 1680 mg (67.8)<br>Polymer (B): 743.1 mg (30.0)<br>Polymerization initiator composition (C): 54 mg (2.2) | 40 | 5 | 3 |
| Ex. 5A | Monomer (A): 1680 mg (58.1)<br>Polymer (B): 1156 mg (40.0)<br>Polymerization initiator composition (C): 54 mg (1.9) | 164 | 5 | 3 |
| Ex. 6A | Monomer (A): 1680 mg (48.4)<br>Polymer (B): 1734 mg (50.0)<br>Polymerization initiator composition (C): 54 mg (1.6) | 2560 | 5 | 3 |
| Comp. Ex. 1A | Monomer (A): 1680 mg (19.4)<br>Polymer (B): 6939 mg (80.0)<br>Polymerization initiator composition (C): 54 mg (0.6) | immeasurable | 1 | 1 |

Evaluation of Flexural Elastic Modulus, Tensile Strength and Flexural Strength

In a 5 ml sample tube, the polymer (B) was weighed in accordance with a blending ratio described in Examples 7A to 9A of the following Table 2. In the sample tube in which the polymer (B) had been weighed, a mixed liquid of the monomer solution (A) and the polymerization initiator composition (C), which had been prepared in a different 1 ml sample tube in accordance with a blending ratio described in Examples 7A to 9A of the following Table 2 similarly to the above, was introduced, and they were mixed together at 25° C. for about 5 seconds using a glass bar so that the mixture might become homogeneous.

The resulting composition was injected into a syringe and immediately filled in a frame to prepare a cured product sample in accordance with the following procedure, as illustrated in FIG. 1. On a glass plate, a sheet of PE Lumirror (trade mark) and a fluororesin frame having a thickness of 0.5 mm (internal size of frame: 25 mm (length)×2 mm (width)) were superposed in this order. In this frame, the composition for hard tissue repair prepared was filled. The filling work was carefully carried out so that bubbles should not be formed. After the filling was completed, a sheet of PE Lumirror (trade mark) and a glass plate were further superposed thereon in this order, and the four corners of the outermost two glass plates were fixed with clips. Thereafter, they were allowed to stand for 24 hours at 25° C. (room temperature), and then the cured product was taken out of the frame. When the resulting cured product had irregularities on the surfaces, the surfaces were abraded with a waterproof abrasive paper #600 to remove irregularities, whereby a cured product was prepared. The resulting cured product had a size of a length of 25 mm, a width of 2 mm and a thickness of 0.5 mm.

Flexural elastic modulus (test rate: 2 mm/min), tensile strength (test rate: 1 mm/min) and flexural strength (test rate: 2 mm/min) of the cured product were determined 24 hours after the preparation by EzTest/CE manufactured by Shimadzu Corporation. The values are each a mean of values obtained by measurements of four times. The evaluation results are set forth in Table 2.

Evaluation of Compression Strength

In a 5 ml sample tube, the polymer (B) was weighed in accordance with a blending ratio described in Examples 7A to 9A of the following Table 2. In the sample tube in which the polymer (B) had been weighed, a mixed liquid of the monomer solution (A) and the polymerization initiator composition (C), which had been prepared in a different 1 ml sample tube in accordance with a blending ratio described in Examples 7A to 9A of the following Table 2 similarly to the above, was introduced, and they were mixed together at 25° C. for about 5 seconds using a glass bar so that the mixture might become homogeneous.

From the resulting composition, a cured product having a size of 4.0 mm×4.0 mm×3.0 mm and a curd product of 6 mm (diameter)×8 mm (length) were prepared. 24 hours after the preparation, compression strength (test rate: 2 m/min) was measured by an Autograph (DSS500 manufactured by Shimadzu Corporation). The results are set forth in Table 2.

TABLE 2

| | Adhesive composition (part(s) by weight) | Flexural elastic modulus (MPa) | Tensile strength (MPa) | Compression strength (MPa) | Flexural strength (MPa) |
|---|---|---|---|---|---|
| Ex. 7A | Monomer (A): 586 mg (66.6) Polymer (B): 262 mg (29.7) Polymerization initiator composition (C): 33 mg (3.7) | 420 | 30 | 55 | 50 |
| Ex. 8A | Monomer (A): 586 mg (51.2) Polymer (B): 525 mg (45.9) Polymerization initiator composition (C): 33 mg (2.9) | 540 | 26 | 60 | 60 |
| Ex. 9A | Monomer (A): 586 mg (32.6) Polymer (B): 1180 mg (65.6) Polymerization initiator composition (C): 33 mg (1.8) | 1500 | 50 | 63 | 67 |

Exothermic Properties

In a 30 ml sample tube, the polymer (B) and barium sulfate (available from Wako Pure Chemical Industries, Ltd.) were weighed in accordance with a blending ratio described in Example 10A. Then, in a 10 ml sample tube, the monomer solution (A) and the polymerization initiator composition (C) were weighed in accordance with a blending ratio described in Example 10A similarly to the above, and they were mixed together. The mixture was introduced into the sample tube in which the polymer (B) had been weighed, and they were mixed together at 25° C. for 1 minute using a glass bar so that the mixture might become homogeneous. Thereafter, the mixture was placed in a cylindrical container having a diameter of 30 mm and a height of 15 mm, and a thermometer was inserted into the central part of the mixture to measure the temperature.

An example of a case where benzoyl peroxide (available from Wako Pure Chemical Industries, Ltd.) was used as a polymerization initiator is shown as Comparative Example 2A. That is to say, in a 100 ml beaker, the polymer (B), barium sulfate and benzoyl peroxide were weighed in accordance with a blending ratio described in Comparative Example 2A. In this beaker, the monomer solution (A) was weighed and introduced, and they were mixed together at 25° C. for 1 minute using a glass bar so that the mixture might become homogeneous. Thereafter, the mixture was placed in a cylindrical container having a diameter of 30 mm and a height of 15 mm, and a thermometer was inserted into the central part of the mixture to measure the temperature.

The results are set forth in Table 3. As for the composition prepared from the monomer (A), the polymer (B) and the polymerization initiator composition (C), the temperature begun to slowly rise immediately after mixing, and the highest temperature was relatively low. On the other hand, in the case of using benzoyl peroxide as a polymerization initiator, a relatively long time was required before the temperature rise, and after the temperature rise begun once, the temperature rapidly rose in a short time. Moreover, the highest temperature was higher than that of the composition prepared from the monomer (A), the polymer (B) and the polymerization initiator composition (C).

TABLE 3

| | Adhesive composition (part(s) by weight) | Temperature |
|---|---|---|
| Ex. 10A | Monomer (A): 20 g (27.7) Polymer (B): 48 g (66.4) Polymerization initiator composition (C): 0.9 g (1.2) Barium sulfate: 3.4 g (4.7) | The temperature gently rose for 5 minutes and 30 seconds after mixing to reach 30° C., thereafter relatively rapidly rose to reach the highest temperature of 60° C. in 7 minutes and 30 seconds after mixing and then slowly lowered. |
| Comp. Ex. 2A | Monomer (A): 20 g (30.6) Polymer (B): 40 g (61.2) Polymerization initiator composition (C): 0.4 g (0.6) Barium sulfate: 5.0 g (7.6) | The temperature hardly rose for 6 minutes after mixing, then gently rose to reach 30° C. in 9 minutes after mixing, thereafter rapidly rose to reach the highest temperature of 85° C. in 9 minutes and 30 seconds after mixing and then slowly lowered. |

Evaluation of Adhesive Strength

Onto a cortical bone surface of the canine femur, an acrylic resin bar having a diameter of 5 mm was fixed at right angles using a composition obtained by mixing the components in accordance with a blending ratio described in Example 10A, and they were immersed in water at 37° C. for 24 hours, followed by carrying out a peel test of the acrylic resin bar from the bone using an Autograph (DSS500 manufactured by Shimadzu Corporation). As a result, the adhesive strength was 10 MPa.

Examples 1B to 13B, Comparative Examples 1B to 13B

In the following examples and comparative examples, the same monomer (A) and the same polymerization initiator composition (C) as in the above examples were used. As the polymer (B), a mixture obtained by mixing the aforesaid polymers (b1), (b2) and (b3) in a blending ratio described in the following Tables 4 to 11 was used. As the X-ray contrast medium, zirconium oxide available from Daiichi Kigenso Kagaku Kogyo Co., Ltd. was used. Mixing of the polymers (b1), (b2) and (b3) with zirconium oxide was carried out by a Turbula shaker (T2C type manufactured by Willy A. Bachofen AG) for 30 minutes at 23±1° C.

Evaluation of Homogeneous Dispersibility

In a polypropylene container having an inner diameter of 2.5 cm and a depth of 1 cm, the polymer (B) and zirconium oxide were weighed in accordance with a blending ratio of Examples 1B to 13B and Comparative Examples 1B to 13B described in the following Tables 4 to 11. In this plastic container, the monomer (A) and the polymerization initiator composition (C), which had been mixed together in a 10 ml glass sample tube in accordance with a blending ratio of Examples 1B to 13B and Comparative Examples 1B to 13B described in the following Tables 4 to 11 similarly to the above, were injected, and they were mixed together by a polypropylene spatula at 25° C. for 20 seconds. Thereafter, the state of the mixture in the container was confirmed by visual observation. The evaluation was carried out in the following manner. A case where a powder of the polymer (B) could not be blended was evaluated to be 0; a case where undissolved lumps of powder were observed was evaluated to be 1; a case where the mixture had no fluidity and was in the clay-like dissolved state was evaluated to be 2; and a case where the mixture had fluidity and was in the dissolved state was evaluated to be 3. The evaluation results are set forth in Table 7. In the case of 0, any test sample could not be prepared, and therefore, other evaluations were not carried out. The evaluation results are set forth in Tables 4 to 11.

Homogeneous Dispersibility of X-Ray Contrast Medium

In a polypropylene container having an inner diameter of 2.5 cm and a depth of 1 cm, the polymer (B) and zirconium oxide were weighed in accordance with a blending ratio of Examples 1B to 13B and Comparative Examples 1B to 13B described in the following Tables 4 to 11 similarly to the above. In this plastic container, the monomer (A) and the polymerization initiator composition (C), which had been mixed together in a 10 ml glass sample tube in accordance with a blending ratio of Examples 1B to 13B and Comparative Examples 1B to 13B described in the following Tables 4 to 11 similarly to the above, were injected, and they were mixed together by a polypropylene spatula at 25° C. for 20 seconds. The state of the mixture in the container was confirmed by visual observation through mixing by spatula and pipetting. The evaluation was carried out in the following manner. A case where precipitation of the X-ray contrast medium in the polymer (B) was observed was evaluated to be 0; a case where precipitation of the X-ray contrast medium was observed but the precipitation came to be unobserved during the stirring of 20 seconds by the spatula was evaluated to be 1; and a case where precipitation of the X-ray contrast medium was not observed from the stirring stage was evaluated to be 2. The evaluation results are set forth in Tables 4 to 11.

Evaluation of Initial Viscosity

In a polypropylene container having an inner diameter of 2.5 cm and a depth of 1 cm, the polymer (B) and zirconium oxide were weighed in accordance with a blending ratio of Examples 1B to 13B and Comparative Examples 1B to 13B described in the following Tables 4 to 11. In this plastic container, the monomer (A) and the polymerization initiator composition (C), which had been mixed together in a 10 ml glass sample tube in accordance with a blending ratio of Examples 1B to 13B and Comparative Examples 1B to 13B described in the following Tables 4 to 11 similarly to the above, were injected, and they were mixed together by a polypropylene spatula at 25° C. for 20 seconds. 60 seconds after mixing, the viscosity was measured at 25° C. by the use of a rheometer (manufactured by HAAKE, RS150). It was confirmed that the viscosity increased with time. The evaluation results are set forth in Tables 4 to 11.

Evaluation of Operability

In a polypropylene container having an inner diameter of 2.5 cm and a depth of 1 cm, the polymer (B) and zirconium oxide were weighed in accordance with a blending ratio of Examples 1B to 13B and Comparative Examples 1B to 13B described in the following Tables 4 to 11. In this plastic container, the monomer (A) and the polymerization initiator composition (C), which had been mixed together in a 10 ml glass sample tube in accordance with a blending ratio of Examples 1B to 13B and Comparative Examples 1B to 13B described in the following Tables 4 to 11 similarly to the above, were injected, and they were mixed together by a polypropylene spatula at 25° C. for 20 seconds. 540 seconds after mixing, the viscosity was measured at 25° C. by the use of a rheometer (manufactured by HAAKE, RS150). It was confirmed that the viscosity increased with time. The evaluation was carried out in the following manner. A case where the viscosity was not less than $80000 \times 10^3$ cP was evaluated to be 0; a case where the viscosity was in the range of $80000 \times 10^3$ cP to $50000 \times 10^3$ cP was evaluated to be 1; a case where the viscosity was in the range of $50000 \times 10^3$ cP to $20000 \times 10^3$ cP was evaluated to be 2; and a case where the viscosity was not more than $20000 \times 10^3$ cP was evaluated to be 3. The evaluation results are set forth in Tables 4 to 11.

Evaluation of Mechanical Properties (1) Flexural Elastic Modulus, Flexural Strength and Tensile Strength In a polypropylene container having an inner diameter of 2.5 cm and a depth of 1 cm, the polymer (B) and zirconium oxide were weighed in accordance with a blending ratio of Example 1B, Example 2B, Example 8B, Comparative Example 1B, Comparative Example 2B, Comparative Example 4B, and Comparative Examples 6B to 9B described in the following Tables 4 to 11. In this plastic container, the monomer (A) and the polymerization initiator composition (C), which had been mixed together in a 10 ml glass sample tube in accordance with a blending ratio of the above examples and comparative examples described in the following Tables 4 to 11 similarly to the above, were injected, and they were mixed together by a polypropylene spatula at 25° C. for 20 seconds. The resulting mixture was immediately filled in a frame to prepare a cured product sample in accordance with the following procedure, as illustrated in FIG. 1. On a glass plate, a sheet of PE Lumirror (trade mark) and a fluororesin frame having a thickness of 0.5 mm (internal size of frame: 25 mm (length)×2 mm (width)) were superposed in this order. In this frame, the composition for hard tissue repair prepared was filled. The filling work was carefully carried out so that bubbles should not be formed. After the filling was completed, a sheet of PE Lumirror (trade mark) and a glass plate were further superposed thereon in this order, and the four corners of the outermost two glass plates were fixed with clips. Thereafter, they were allowed to stand for 24 hours at 25° C. (room temperature), and then the cured product was taken out of the frame. When the resulting cured product had irregularities on the surfaces, the surfaces were abraded with a waterproof abrasive paper #600 to remove irregularities, whereby a cured product was prepared. The resulting cured product had a size of a length of 25 mm, a width of 2 mm and a thickness of 0.5 mm.

24 hours after the preparation, flexural elastic modulus (test rate: 2 mm/min), flexural strength (test rate: 2 mm/min) and tensile strength (test rate: 1 mm/min) of the cured product were determined by an Autograph (EZ-S manufactured by Shimadzu Corporation). The values are each a mean of values obtained by measurements of four times. The evaluation results are set forth in Tables 4 to 11.

The evaluation was carried out in the following manner. A case where the flexural elastic modulus was not less than 1800 MPa, the flexural strength was not less than 50 MPa, and the tensile strength was not less than 30 MPa was regarded as pass. A case where the X-ray contrast medium was not homogeneously dispersed and any specimen of a homogenous cured product was not obtained was regarded as immeasurable. The evaluation results are set forth in Tables 4 to 11.

(2) Evaluation of Compression Strength

Figure 2:
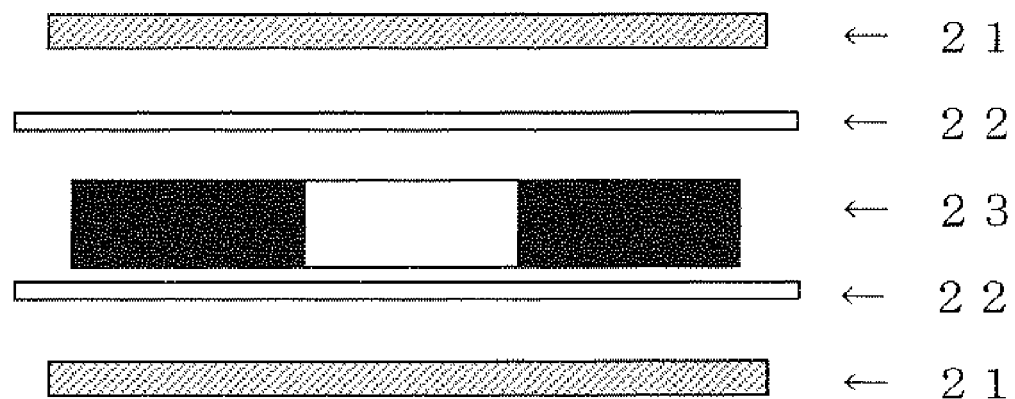
FIG. 2 is a schematic view showing an example of a process for preparing a sample of a cured product used in the examples (compression strength) of the present invention.

In a polypropylene container having an inner diameter of 2.5 cm and a depth of 1 cm, the polymer (B) and zirconium oxide were weighed in accordance with a blending ratio of Example 2B, Example 8B, Comparative Example 1B, Comparative Example 2B and Comparative Example 6B described in the following Tables 4 to 11. In this plastic container, the monomer (A) and the polymerization initiator composition (C), which had been mixed together in a 10 ml glass sample tube in accordance with a blending ratio of the above examples and comparative examples described in the following Tables 4 to 11 similarly to the above, were injected, and they were mixed together by a polypropylene spatula at 25° C. for 20 seconds. On a glass plate, a sheet of PE Lumirror (trade mark) and a silicon resin frame having a thickness of 5 mm (internal size of frame: 10 mm (length)×10 mm (width)) were superposed in this order as illustrated in FIG. 2. In this frame, the composition for hard tissue repair prepared was filled. The filling work was carefully carried out so that bubbles should not be formed. After the filling was completed, a sheet of PE Lumirror (trade mark) and a glass plate were further superposed thereon in this order, and a weight of 200 g was placed on the top. Thereafter, they were allowed to stand for 24 hours at 25° C. (room temperature), then the cured product was taken out of the frame, and thus, a cured product was prepared. When the resulting cured product had irregularities on the surfaces, the surfaces were abraded with a waterproof abrasive paper #600 to remove irregularities. 24 hours after the preparation, compression strength of the cured product was measured by a precision universal testing machine (2100 type manufactured by Intesco Co., Ltd.) at a test rate of 2 mm/min and at 23±1° C. The evaluation was carried out in the following manner. A case where the compression strength was not less than 70 MPa was regarded as pass. A case where no yield point was observed was regarded as immeasurable. The evaluation results are set forth in Tables 4 to 11.

Overall Evaluation

A case where the homogeneous dispersibility was not less than 2, the homogeneous dispersibility of the X-ray contrast medium was not less than 1, the initial viscosity, i.e., viscosity after 60 seconds, was in the range of 10 to 2,000,000 cP, the operability was 3, and the mechanical properties were regarded as pass was evaluated to be AA; a case where the solubility was not less than 1, the homogeneity of dissolution was not less than 1, the viscosity after 60 seconds was in the range of 10 to 2,000,000 cP, the operability was not less than 2, and the mechanical properties were regarded as pass was evaluated to be A; a case where the solubility was not less than 1, the homogeneity of dissolution was not less than 1, the viscosity after 60 seconds was in the range of 10 to 2,000,000 cP, the operability was not less than 1, and the mechanical properties were regarded as pass was evaluated to be B; a case where the solubility was 0, or a case where the homogeneity of dissolution was 0, or a case where the viscosity after 60 seconds was out of the range of 10 to 2,000,000 cP, or a case where the operability was 0, or a case where the mechanical properties were regarded as failure was evaluated to be C. The evaluation results are set forth in Tables 4 to 11.

TABLE 4

| | Composition for hard tissue repair (part(s) by weight) | Stirrability | Stirring homogeneity | Initial viscosity (×10³ cP) | Operability Evaluation | Viscosity (×10³ cP) | Mechanical properties (MPa) Flexural elastic modulus | Flexural strength | Tensile strength | Compression strength | Overall evaluation |
|---|---|---|---|---|---|---|---|---|---|---|---|
| Ex. 1B | Monomer (A): 560 mg (58.4) Polymer (B): 363.5 mg (37.9) (b1): 87.5% (b2): 0% (b3): 12.5% Polymerization initiator composition (C): 35 mg (3.7) Zirconium oxide: 363.5 mg | 3 | 1 | 150 | 3 | 5000 | | | | | AA |
| Ex. 2B | Monomer (A): 560 mg (53.8) Polymer (B): 446.5 mg (42.9) (b1): 25.0% (b2): 62.5% (b3): 12.5% Polymerization initiator composition (C): 35 mg (3.3) Zirconium oxide: 446.5 mg | 3 | 2 | 2.8 | 3 | 280 | pass 2660 | pass 59 | pass 45 | pass 114 | AA |
| Ex. 3B | Monomer (A): 560 mg (53.8) Polymer (B): 446.5 mg (42.9) (b1): 75.0% (b2): 25.0% (b3): 0% Polymerization initiator composition (C): 35 mg (3.3) Zirconium oxide: 446.5 mg | 3 | 2 | 58 | 3 | 5500 | | | | | AA |

TABLE 4-continued

| Composition for hard tissue repair (part(s) by weight) | Stirrability | Stirring homogeneity | Initial viscosity (×10³ cP) | Operability Evaluation | Viscosity (×10³ cP) | Mechanical properties (MPa) Flexural elastic modulus | Flexural strength | Tensile strength | Compression strength | Overall evaluation |
|---|---|---|---|---|---|---|---|---|---|---|
| Ex. 4B | Monomer (A): 560 mg (53.8) Polymer (B): 446.5 mg (42.9) (b1): 87.5% (b2): 0% (b3): 12.5% Polymerization initiator composition (C): 35 mg (3.4) Zirconium oxide: 446.5 mg | 3 | 2 | 444 | 3 | 14800 | | | | | AA |

Notes:
(b1) + (b2) + (b3) = 100% "%" of (b1) to (b3) means "% by weight".

The same shall apply in Table 5 to 11.

TABLE 5

| Composition for hard tissue repair (part(s) by weight) | Stirrability | Stirring homogeneity | Initial viscosity (×10³ cP) | Operability Evaluation | Viscosity (×10³ cP) | Mechanical properties (MPa) Flexural elastic modulus | Flexural strength | Tensile strength | Compression strength | Overall evaluation |
|---|---|---|---|---|---|---|---|---|---|---|
| Ex. 5B | Monomer (A): 560 mg (48.8) Polymer (B): 552.5 mg (48.1) (b1): 50.0% (b2): 0% (b3): 50.0% Polymerization initiator composition (C): 35 mg (3.1) Zirconium oxide: 552.5 mg | 3 | 2 | 50 | 3 | 7900 | | | | | AA |
| Ex. 6B | Monomer (A): 560 mg (48.8) Polymer (B): 552.5 mg (48.1) (b1): 62.5% (b2): 0% (b3): 37.5% Polymerization initiator composition (C): 35 mg (3.1) Zirconium oxide: 552.5 mg | 3 | 2 | 140 | 3 | 13000 | | | | | AA |
| Ex. 7B | Monomer (A): 560 mg (48.8) Polymer (B): 552.5 mg (48.1) (b1): 75.0% (b2): 0% (b3): 25.0% Polymerization initiator composition (C): 35 mg (3.1) Zirconium oxide: 552.5 mg | 3 | 2 | 500 | 2 | 24200 | | | | | A |

TABLE 5-continued

| Composition for hard tissue repair (part(s) by weight) | Stirrability | Stirring homogeneity | Initial viscosity ($\times 10^3$ cP) | Operability Evaluation | Viscosity ($\times 10^3$ cP) | Flexural elastic modulus | Flexural strength | Tensile strength | Compression strength | Overall evaluation |
|---|---|---|---|---|---|---|---|---|---|---|
| Ex. 8B | Monomer (A): 560 mg (43.4) Polymer (B): 694 mg (53.8) (b1): 25.0% (b2): 62.5% (b3): 12.5% Polymerization initiator composition (C): 35 mg (2.8) Zirconium oxide: 694 mg | 3 | 2 | 76 | 2 | 33000 | pass 3130 | pass 66 | pass 48 | pass 121 | A |

TABLE 6

| | Composition for hard tissue repair (part(s) by weight) | Stirrability | Stirring homogeneity | Initial viscosity ($\times 10^3$ cP) | Operability Evaluation | Viscosity ($\times 10^3$ cP) | Flexural elastic modulus | Flexural strength | Tensile strength | Compression strength | Overall evaluation |
|---|---|---|---|---|---|---|---|---|---|---|---|
| Ex. 9B | Monomer (A): 560 mg (43.4) Polymer (B): 694 mg (53.8) (b1): 25.0% (b2): 0% (b3): 75.0% Polymerization initiator composition (C): 35 mg (2.8) Zirconium oxide: 694 mg | 3 | 2 | 29 | 3 | 7100 | | | | | AA |
| Ex. 10B | Monomer (A): 560 mg (43.4) Polymer (B): 694 mg (53.8) (b1): 37.5% (b2): 62.5% (b3): 0% Polymerization initiator composition (C): 35 mg (2.8) Zirconium oxide: 694 mg | 3 | 2 | 267 | 1 | 52000 | | | | | B |
| Ex. 11B | Monomer (A): 560 mg (43.4) Polymer (B): 694 mg (53.8) (b1): 37.5% (b2): 0% (b3): 62.5% Polymerization initiator composition (C): 35 mg (2.8) Zirconium oxide: 694 mg | 3 | 2 | 110 | 3 | 8400 | | | | | AA |

TABLE 7

| Composition for hard tissue repair (part(s) by weight) | Stirrability | Stirring homogeneity | Initial viscosity (×10³ cP) | Operability Evaluation | Viscosity (×10³ cP) | Mechanical properties (MPa) Flexural elastic modulus | Flexural strength | Tensile strength | Compression strength | Overall evaluation |
|---|---|---|---|---|---|---|---|---|---|---|
| Ex. 12B | Monomer (A): 560 mg (43.4) Polymer (B): 694 mg (53.8) (b1): 50.0% (b2): 0% (b3): 50.0% Polymerization initiator composition (C): 35 mg (2.8) Zirconium oxide: 694 mg | 3 | 2 | 179 | 2 | 47800 | | | | | A |
| Ex. 13B | Monomer (A): 560 mg (37.6) Polymer (B): 892.5 mg (60.0) (b1): 25.0% (b2): 0% (b3): 75.0% Polymerization initiator composition (C): 35 mg (2.4) Zirconium oxide: 892.5 mg | 3 | 2 | 270 | 1 | 69680 | | | | | B |

TABLE 8

| Composition for hard tissue repair (part(s) by weight) | Stirrability | Stirring homogeneity | Initial viscosity (×10³ cP) | Operability Evaluation | Viscosity (×10³ cP) | Mechanical properties (MPa) Flexural elastic modulus | Flexural strength | Tensile strength | Compression strength | Overall evaluation |
|---|---|---|---|---|---|---|---|---|---|---|
| Comp. Ex. 1B | Monomer (A): 560 mg (77.5) Polymer (B): 127.5 mg (17.6) (b1): 100% (b2): 0% (b3): 0% Polymerization initiator composition (C): 35 mg (4.9) Zirconium oxide: 127.5 mg | 3 | 0 | | | | failure 1780 | failure 42 | pass 37 | pass 85 | C |
| Comp. Ex. 2B | Monomer (A): 560 mg (70.6) Polymer (B): 198.5 mg (25.0) (b1): 100% (b2): 0% (b3): 0% Polymerization initiator composition (C): 35 mg (4.4) Zirconium oxide: 198.5 mg | 3 | 0 | 1.7 | 3 | 64 | pass 2200 | pass 51 | pass 41 | immeasurable | C |

TABLE 8-continued

| | Composition for hard tissue repair (part(s) by weight) | Stirrability | Stirring homogeneity | Initial viscosity (×10³ cP) | Operability Evaluation | Viscosity (×10³ cP) | Flexural elastic modulus | Mechanical properties (MPa) Flexural strength | Tensile strength | Compression strength | Overall evaluation |
|---|---|---|---|---|---|---|---|---|---|---|---|
| Comp. Ex. 3B | Monomer (A): 560 mg (62.7) Polymer (B): 297.5 mg (33.3) (b1): 0% (b2): 100% (b3): 0% Polymerization initiator composition (C): 35 mg (4.0) Zirconium oxide: 297.5 mg | 3 | 0 | 0.06 | 3 | 10 | | | | | C |
| Comp. Ex. 4B | Monomer (A): 560 mg (62.7) Polymer (B): 297.5 mg (33.3) (b1): 25.0% (b2): 62.5% (b3): 12.5% Polymerization initiator composition (C): 35 mg (4.0) Zirconium oxide: 297.5 mg | 3 | 0 | 0.4 | 3 | 36 | pass 2670 | pass 60 | pass 45 | | C |

TABLE 9

| | Composition for hard tissue repair (part(s) by weight) | Stirrability | Stirring homogeneity | Initial viscosity (×10³ cP) | Operability Evaluation | Viscosity (×10³ cP) | Flexural elastic modulus | Mechanical properties (MPa) Flexural strength | Tensile strength | Compression strength | Overall evaluation |
|---|---|---|---|---|---|---|---|---|---|---|---|
| Comp. Ex. 5B | Monomer (A): 560 mg (62.7) Polymer (B): 297.5 mg (33.3) (b1): 100% (b2): 0% (b3): 0% Polymerization initiator composition (C): 35 mg (4.0) Zirconium oxide: 297.5 mg | 3 | 0 | 11 | 3 | 2400 | | | | | C |
| Comp. Ex. 6B | Monomer (A): 560 mg (53.8) Polymer (B): 446.5 mg (42.9) (b1): 100% (b2): 0% (b3): 0% Polymerization initiator composition (C): 35 mg (3.3) Zirconium oxide: 446.5 mg | 3 | 2 | 700 | 0 | 81000 | pass 2710 | pass 64 | pass 57 | pass 110 | C |

TABLE 9-continued

| | Composition for hard tissue repair (part(s) by weight) | Stirrability | Stirring homogeneity | Initial viscosity (×10³ cP) | Operability Evaluation | Viscosity (×10³ cP) | Mechanical properties (MPa) Flexural elastic modulus | Flexural strength | Tensile strength | Compression strength | Overall evaluation |
|---|---|---|---|---|---|---|---|---|---|---|---|
| Comp. Ex. 7B | Monomer (A): 560 mg (43.4) Polymer (B): 694 mg (53.8) (b1): 0% (b2): 100% (b3): 0% Polymerization initiator composition (C): 35 mg (2.8) Zirconium oxide: 694 mg | 3 | 0 | 70 | 0 | 106500 | pass 5480 | pass 93 | pass 41 | | C |
| Comp. Ex. 8B | Monomer (A): 560 mg (43.4) Polymer (B): 694 mg (53.8) (b1): 0% (b2): 0% (b3): 100% Polymerization initiator composition (C): 35 mg (2.8) Zirconium oxide: 694 mg | 3 | 0 | 1.5 | 3 | 110 | pass 8683 | pass 103 | immeasurable | | C |

TABLE 10

| | Composition for hard tissue repair (part(s) by weight) | Stirrability | Stirring homogeneity | Initial viscosity (×10³ cP) | Operability Evaluation | Viscosity (×10³ cP) | Mechanical properties (MPa) Flexural elastic modulus | Flexural strength | Tensile strength | Compression strength | Overall evaluation |
|---|---|---|---|---|---|---|---|---|---|---|---|
| Comp. Ex. 9B | Monomer (A): 560 mg (43.4) Polymer (B): 694 mg (53.8) (b1): 100% (b2): 0% (b3): 0% Polymerization initiator composition (C): 35 mg (2.8) Zirconium oxide: 694 mg | 2 | 2 | 4000 | 0 | 859300 | pass 3330 | pass 78 | pass 110 | | C |
| Comp. Ex. 10B | Monomer (A): 560 mg (37.6) Polymer (B): 892.5 mg (60.0) (b1): 0% (b2): 100% (b3): 0% Polymerization initiator composition (C): 35 mg (2.4) Zirconium oxide: 892.5 mg | 3 | 2 | 31 | 0 | 99320 | | | | | C |

TABLE 10-continued

| Composition for hard tissue repair (part(s) by weight) | Stirrability | Stirring homo-geneity | Initial viscosity ($\times 10^3$ cP) | Operability Evaluation | Viscosity ($\times 10^3$ cP) | Flexural elastic modulus | Mechanical properties (MPa) Flexural strength | Tensile strength | Compression strength | Overall evaluation |
|---|---|---|---|---|---|---|---|---|---|---|
| Comp. Ex. 11B | Monomer (A): 560 mg (31.4) Polymer (B): 1190 mg (66.7) (b1): 0% (b2): 100% (b3): 0% Polymerization initiator composition (C): 35 mg (1.9) Zirconium oxide: 1190 mg | 0 | | | | | | | | C |

TABLE 11

| Composition for hard tissue repair (part(s) by weight) | Stirrability | Stirring homo-geneity | Initial viscosity ($\times 10^3$ cP) | Operability Evaluation | Viscosity ($\times 10^3$ cP) | Flexural elastic modulus | Mechanical properties (MPa) Flexural strength | Tensile strength | Compression strength | Overall evaluation |
|---|---|---|---|---|---|---|---|---|---|---|
| Comp. Ex. 12B | Monomer (A): 560 mg (31.4) Polymer (B): 1190 mg (66.7) (b1): 0% (b2): 0% (b3): 100% Polymerization initiator composition (C): 35 mg (1.9) Zirconium oxide: 1190 mg | 0 | | | | | | | | C |
| Comp. Ex. 13B | Monomer (A): 560 mg (31.4) Polymer (B): 1190 mg (66.7) (b1): 100% (b2): 0% (b3): 0% Polymerization initiator composition (C): 35 mg (1.9) Zirconium oxide: 1190 mg | 0 | | | | | | | | C |

REFERENCE SIGNS LIST

11: glass plate, 12: Lumirror (trade mark), 13: fluororesin frame (the central white part indicates a space of 25 mm (length)×2 mm (width), and this part is filled with a mixed liquid of the monomer solution (A), the polymer (B) and the polymerization initiator composition (C).)

21: glass plate, 22: Lumirror (trade mark), 23: silicon resin frame (the central white part indicates a space of 10 mm (length)×10 mm (width)×5 mm (thickness), and this part is filled with a mixed liquid of the monomer solution (A), the polymer (B) and the polymerization initiator composition (C).)

The invention claimed is:

1. A composition for hard tissue repair, comprising 24 to 58.4 parts by weight of a monomer (A), 37.9 to less than 65 parts by weight of a (meth)acrylate polymer (B) and 0.5 to 10 parts by weight of a polymerization initiator composition (C) containing an organoboron compound (c1), with the proviso that the total amount of the components (A), (B) and (C) is 100 parts by weight, and 10 to 70 parts by weight of an x-ray contrast medium, based on 100 parts by weight of the total weight of components (A), (B) and (C), wherein polymer (B) is a polymer mixture which comprises polymer particles (b1) having a weight-average molecular weight of $30 \times 10^4$ to $60 \times 10^4$ and a specific surface area of 1.5 to 4.5 m$^2$/g, polymer particles (b2) having a weight-average molecular weight of $5 \times 10^4$ to $20 \times 10^4$ and a specific surface area of 0.51 to 1.2 m$^2$/g and polymer particles (b3) having a weight-average molecular weight of $5 \times 10^4$ to $20 \times 10^4$ and a specific surface area of 0.1 to 0.5 m$^2$/g, wherein (b1) is present in an amount of 20 to 98% by weight, (b2) is present in an amount of 2 to 80% by weight and (b3) is present in an amount of 2 to 80% by weight based on a total weight of the polymer particles (b1), (b2) and (b3), with the proviso that the total amount of polymer particles (b1), (b2) and (b3) is 100% by weight.

2. The composition for hard tissue repair of claim 1, wherein the polymerization initiator composition (C) contains an aprotic solvent (c2) having a boiling point of 30° C. to 150° C. in an amount of 30 to 80 parts by weight based on 100 parts by weight of the organoboron compound (c1).

3. The composition for hard tissue repair of claim 1, wherein the polymerization initiator composition (C) contains an aprotic solvent (c2') having a boiling point of 50° C. to 120° C. in an amount of 5 to 40 parts by weight and an alcohol (c3) having a boiling point of 60° C. to 180° C. in an amount of 0.2 to 5 parts by weight, based on 100 parts by weight of the organoboron compound (c1).

4. The composition for hard tissue repair of claim 1, which has a viscosity of 0.4 to 2,000,000 cp within 30 seconds after mixing components (A), (B) and (C).

5. The composition for hard tissue repair of claim 1, which further comprises a polymerization inhibitor (D).

6. The composition for hard tissue repair of claim 5, wherein the amount of the polymerization inhibitor (D) is in the range of 10 to 5000 ppm based on monomer (A).

7. The composition for hard tissue repair of claim 5, wherein the polymerization inhibitor (D) is at least one substance selected from hydroquinone, dibutylhydroquinone, hydroquinone monomethyl ether, 2,6-di-tert-butylphenol, 2,6-di-tert-butyl-p-cresol, catechol, pyrogallol, benzoquinone, 2-hydroxybenzoquinone, p-methoxyphenol, t-butylcatechol, butylated hydroxyanisole, butylated hydroxytoluene and t-butylhydroquinone.

8. The composition for hard tissue repair of claim 1, which further comprises an ultraviolet light absorber.

9. The composition for hard tissue repair of claim 1, which further comprises at least one substance selected from a flexibilizer and a plasticizer.

10. The composition for hard tissue repair of claim 1, which further comprises at least one substance selected from: anti-infectious agents, antibiotics, antibacterial agents, anti-virus agents, analgesics, anorectic drugs, antihelmintic drugs, antiarthritic drugs, antiasthmatic drugs, anticonvulsants, antidepressants, antidiuretics, antidiarrheal agents, antihistamine drugs, anti-inflammatory drugs, antimigraine drugs, antiemetic agents, antineoplastic drugs, antiparkinsonian agents, antipruritic drugs, antipsychotics, antipyretic drugs, antispasmodic drugs, anticholinergic agents, sympathomimetic agents, cardiovascular drugs, antiarrhythmic drugs, antihypertensive drugs, diuretics, vasodilators, immunosuppressant drugs, muscle-relaxant drugs, parasympatholytic drugs, stimulants, sedative drugs, tranquilizers, cholinergic agents, chemotherapeutic drugs, radio pharmaceuticals, bone inductive drugs, heparin neutralizer agents of static bladder, procoagulants, hemostatic agents, xanthine derivatives, hormones, proteins of natural origin or proteins synthesized by genetic engineering, polysaccharides, glycoproteins, lipoproteins, oligonucleotides, antibody, antigen, vasopressin, vasopressin analogs, epinephrine, selectin, clot promoting toxicants, plasminogen activating factor inhibitors, platelet activators, bone-forming factors, synthetic peptides having hemostatic action,
orange oil, grapefruit oil, lemon oil, lime oil, clove oil, wintergreen oil, peppermint oil, peppermint spirit, banana distillate, cucumber distillate, honey distillate, rose water, menthol, anethole, alkyl salicylate, benzaldehyde, monosodium glutamate, ethylvanillin, thymol and vanillin.

11. A kit for hard tissue repair containing the composition of claim 1, in which monomer (A), (meth)acrylate polymer (B) and the polymerization initiator composition (C), are encased in two or more divided groups.

12. The kit for hard tissue repair of claim 11, in which monomer (A), polymer (B) and the polymerization initiator composition (C) are each independently encased, and monomer (A) is first mixed with the polymerization initiator composition (C) and subsequently mixed with polymer (B).

13. A kit for hard tissue repair containing the composition of claim 5, in which monomer (A), (meth)acrylate polymer (B), the polymerization initiator composition (C) and the polymerization inhibitor (D), are encased in two or more divided groups.

14. The kit for hard tissue repair of claim 13, in which a mixture of monomer (A) and the polymerization inhibitor (D); polymer (B) and the polymerization initiator composition (C) are each independently encased, and the mixture of monomer (A) and the polymerization inhibitor (D) is first mixed with the polymerization initiator composition (C) and subsequently mixed with polymer (B).

15. The kit for hard tissue repair of claim 11, which includes a jig that is used for applying a composition for hard tissue repair obtained by mixing components (A), (B) and (C) to an affected part.

16. The kit for hard tissue repair of claim 15, wherein the jig is at least one jig selected from a brush, a fiber ball, a cloth, a sponge ball and a piece of sponge.

17. The kit for hard tissue repair of claim 11, which further contains an aqueous solution for pretreatment containing 1 to 15% by weight of citric acid and 1 to 5% by weight of iron(III) chloride.

18. The kit for hard tissue repair of claim 13, which includes a jig that is used for applying a composition for hard tissue repair obtained by mixing components (A), (B), (C) and (D) to an affected part.

19. The kit for hard tissue repair of claim 13, which further contains an aqueous solution for pretreatment containing 1 to 15% by weight of citric acid and 1to 5% by weight of iron(III) chloride.

20. The composition for hard tissue repair of claim 1, wherein the composition has a viscosity of 10 to 80,000,000 cp, at 540 seconds after mixing components (A), (B) and (C).

* * * * *